United States Patent
Dreyfuss et al.

(10) Patent No.: US 8,822,168 B2
(45) Date of Patent: Sep. 2, 2014

(54) ASSAYS FOR DETECTING SMALL NUCLEAR RIBONUCLEOPROTEIN PARTICLE ASSEMBLY AND SURVIVAL OF MOTOR NEURONS ACTIVITY

(75) Inventors: Gideon Dreyfuss, Wynnewood, PA (US); Lili Wan, Edison, NJ (US); Elizabeth Ottinger, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1031 days.

(21) Appl. No.: 11/372,619

(22) Filed: Mar. 10, 2006

(65) Prior Publication Data

US 2006/0223092 A1 Oct. 5, 2006

Related U.S. Application Data

(60) Provisional application No. 60/660,634, filed on Mar. 11, 2005.

(51) Int. Cl.
| | |
|---|---|
| C12Q 1/28 | (2006.01) |
| C12Q 1/68 | (2006.01) |
| G01N 33/53 | (2006.01) |
| G01N 33/543 | (2006.01) |
| G01N 33/567 | (2006.01) |
| G01N 33/68 | (2006.01) |
| G01N 33/50 | (2006.01) |
| C07K 16/18 | (2006.01) |

(52) U.S. Cl.
CPC ........ *G01N 33/5058* (2013.01); *G01N 2500/00* (2013.01); *G01N 33/6893* (2013.01); *G01N 33/502* (2013.01); *G01N 33/68* (2013.01); *C12Q 1/6804* (2013.01); *G01N 33/5008* (2013.01)

USPC .......... 435/7.95; 435/6.1; 435/6.19; 435/7.1; 435/7.21; 435/7.5; 435/7.8; 435/28; 435/91.21; 435/91.3; 435/91.51; 436/503; 436/506; 436/507; 436/508; 436/518; 436/524; 436/528; 436/172; 530/388.2; 530/389.1; 530/391.1; 530/391.3

(58) Field of Classification Search
USPC ........ 424/810; 435/6, 7.5, 91.21, 91.3, 91.31, 435/91.51, 6.1, 6.19, 7.1, 7.21, 7.8, 7.95, 435/28; 436/506–508, 503, 518, 524, 528, 436/172; 530/388.2, 389.1, 391.1, 391.3
See application file for complete search history.

(56) References Cited

U.S. PATENT DOCUMENTS

| | | | | |
|---|---|---|---|---|
| 4,668,624 | A * | 5/1987 | Roberts | 435/70.3 |
| 6,168,931 | B1 * | 1/2001 | Swartz et al. | 435/68.1 |
| 6,579,681 | B1 * | 6/2003 | Huls et al. | 435/6 |
| 6,994,986 | B2 * | 2/2006 | Swartz et al. | 435/68.1 |
| 7,138,236 | B1 * | 11/2006 | Jackson et al. | 435/7.1 |
| 2006/0234242 | A1 * | 10/2006 | Cheatham et al. | 435/6 |

OTHER PUBLICATIONS

Jurica, M.S. et al. Purification and characterization of native spliceosomes suitable for three-dimensional structural analysis. RNA. 2002;8:426-439.*

Lock, R.J. & Unsworth, D.J. Antibodies to extractable nuclear antigens. Has technological drift affected clinical interpretation? J. Clin. Pathol. 2001;54:187-190.*

(Continued)

*Primary Examiner* — Gail R Gabel
*Assistant Examiner* — James L Grun
(74) *Attorney, Agent, or Firm* — Riverside Law LLP

(57) ABSTRACT

The present invention includes assays and kits for detecting the assembly of an RNA binding protein-RNA complex and for detecting the activity of an RNA binding protein.

9 Claims, 14 Drawing Sheets

(56) References Cited

OTHER PUBLICATIONS

Hasegawa, H. et al. Anti-Sm autoantibodies cross-react with ribosomal protein S10. Arthritis Rheumatism. 1998;41:1040-1046.*
Petrovas, C.J. et al. A major Sm epitope anchored to sequential oligopeptide carriers is a suitable antigenic substrate to detect anti-Sm antibodies. J. Immunol. Methods. 1998;220:59-68.*
Fisher, D.E. et al. Synthesis and assembly of human small nuclear ribonucleoproteins generated by cell-free translation. Proc. Natl. Acad. Sci. USA. 1983;80:6356-6360.*
Tan, E.M. & Kunkel, H.G. Characteristics of a soluble nuclear antigen precipitating with sera of patients with systemic lupus erythematosus. J. Immunol. 1966;96:464-471.*
Ross et al., 1997. Characterization of a Beta-actin mRNA Zipcode-binding protein. Molecular and Cellular Biology 17: 2158-2165.*
Liu et al., 1996. Molecular Characterization of the protein products of the Fragile X Symdrome gene and the Survival of Motor Neurons gene. Cold Spring Harbor Symposia on Quantitative Biology 61: 689-697.*
Lorson et al., 1998. The domain encoded by exon 2 of the survival motor neuron protein mediates nucleic acid binding. Human Molecular Genetics 7: 1269-1275.*
Achsel, et al., "The Sm Domain is an Ancient RNA-Binding Motif with Oligo(U) Specificity," *Proc Natl Acad Sci USA*, vol. 98, pp. 3685-3689, 2001.
Bird et al., "Single-Chain Antigen-Binding Proteins," *Science*, vol. 242, pp. 423-426, 1988.
Branlant, et al., "U2 RNA Shares a Structural Domain with U1, U4, and U5 RNAs," *Embo Journal*, vol. 1, pp. 1259-1265, 1982.
Buhler, et al., "Essential Role for the Tudor Domain of SMN in Spliceosomal U snRNP Assembly: Implications for Spinal Muscular Atrophy," *Human Molecular Genetics*, vol. 8, pp. 2351-2357, 1999.
Charroux, et al., "Gemin3: A Novel DEAD Box Protein that Interacts with SMN the Spinal Muscular Atrophy Gene Product, and is a Component of Gems," *J. Cell Biol*, vol. 147: 1181-1193, 1999.
Charroux, et al., "Gemin4: A Novel Component of SMN Complex that is Found ijn both Gems and Nucleoli," *J. Cell Biol*, vol. 148, pp. 1177-1186, 2000.
Cifuentes-Diaz, et al., "Spinal Muscular Atrophy," *Semin Pediatr Neurol*, vol. 9, pp. 145-150, 2002.
Coovert, et al., "The Survival Motor Neuron Protein in Spinal Muscular Atrophy," *Human Molecular Genetics*, vol. 6, pp. 1205-1214, 1997.
Crawford et al., "The Neurobiology of Childhood Spinal Muscular Atrophy," *Neurobiology of Disease*, vol. 3, pp. 97-110, 1996.
Fischer et al., "An Essential Signaling Role for the m3G Cap in the Transport of U1 snRNP to the Nucleus," *Science*, vol. 249, pp. 786-790, 1990.
Fischer, et al., "Nucleo-Cytoplasmic Transport of U snRNPs: Definition of a Nuclear Location Signal in the Sm Core Domain that Binds a Transport Receptor Independently of the $m_3G$ Cap," *EMBO Journal*, vol. 12: 573-583, 1993.
Fischer, et al., "The SMN-SIP1 Complex has an Essential Role in Spliceosomal snRNP Biogenesis," *Cell*, vol. 90, pp. 1023-1029, 1997.
Gubitz, et al., "Gemin5, a Novel WD Repeat Protein Component of the SMN Complex that Binds Sm Proteins," *Journal of Biological Chemistry*, vol. 277, pp. 5631-5636, 2002.
Hamm, et al., "In Vitro Assembly of U1 snRNPs," *EMBO Journal*, vol. 6, pp. 3479-3485, 1987.
Hamm, et al., "The Trimethylguanosine Cap Structure of U1 snRNA is a Component of a Bipartite Nuclear Targeting Signal," *Cell*, vol. 62, pp. 569-577, 1990.
Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, vol. 85, pp. 5879-5883, 1988.
Iannaccone, et al., "Spinal Muscular Atrophy," *Current Neurology Neuroscience Reports*, vol. 4(1), pp. 74-80, 2004.
Jarmolowski, et al., "The Determinants for Sm Protein Binding to Xenopus U1 and U5 snRNAs are Complex and Non-Identical," EMBO Journal, vol. 12, pp. 223-232, 1993.

Kambach, et al., "Crystal Structures of Two Sm Protein Complexes and Their Implications for the Assembly of the Spliceosomal snRNPs," *Cell*, vol. 96, pp. 375-387, 1999.
Kambach, et al., "Structure and Assembly of the Spliceosomal Small Nuclear Ribonucleoprotein Particles," *Curr Opin Struct Biol*, vol. 9, pp. 222-230, 1999.
Kataoka, et al., "Pre-mRNA Splicing Imprints mRNA in the Nucleus with a Novel RNA-Binding Protein that Persists in the Cytoplasm," *Mol Cell*, vol. 6, pp. 673-682, 2000.
Kleinschmidt, et al., "U2 Small Nuclear RNP Assembly In Vitro," *Nucleic Acids Research*, vol. 17, pp. 4817-4828, 1989.
Lefebvre, et al., "Identification and Characterization of a Spinal Muscular Atrophy-Determining Gene," *Cell*, vol. 80, pp. 155-165, 1995.
Lefebvre, et al., "Correlation Between Severity and SMN Protein Level in Spinal Muscular Atrophy," *Nature Genetics*, vol. 16, pp. 265-269, 1997.
Lerner, et al., "Monoclonal Antibodies to Nucleic Acid-Containing Cellular Constituents: Probes for Molecular Biology and Autoimmune Disease," *Proc Natl Acad Sci USA*, vol. 78, pp. 2737-2741, 1981.
Luhrmann, "Functions of U-snRNPs," *Molecular Biology Reports*, vol. 14, pp. 183-192, 1990.
Luhrmann, et al., "Structure of Spliceosomal snRNPs and Their Role in Pre-mRNA Splicing," *Biochim Biophys Acta*, vol. 1087, pp. 265-292, 1990.
Mattaj, "Cap Trimethylation of U snRNA is Cytoplasmic and Dependent on U snRNP Protein Binding," *Cell*, vol. 46, pp. 905-911, 1986.
Mattaj, et al., "Nucleocytoplasmic Transport and snRNP Assembly," *Molecular Biology Report*, vol. 18, pp. 79-83, 1993.
Meister, et al., "A Multiprotein Complex Mediates the ATP-Dependent Assembly of Spliceosomal U snRNPs," *Nat Cell Biol*, vol. 3, pp. 945-949, 2001.
Meister et al., "Assisted RNP Assembly: SMN and PRMT5 Complexes Cooperate in the Formation of Spliceosomal UsnRNPs," *EMBO Journal*, vol. 21, pp. 5853-5863, 2002.
Nilsen, "The Spliceosome: The Most Complex Macromolecular Machine in the Cell?" *Bioessays*, vol. 5, pp. 1147-1149, 2003.
Patel et al., "Splicing Double: Insights from the Second Spliceosome," *Nat Rev Mol Cell Biol.*, vol. 4, pp. 960-970, 2003.
Pellizzoni et al. "Essential Role for the SMN Complex in the Specificity of snRNP Assembly," *Science*, vol. 298, pp. 1775-1779, 2002.
Pisetsky et al., "Idiotypic Analysis of a Monoclonal Anti-Sm Antibody," *Journal of Immunology*, vol. 129, pp. 1489-1492, 1982.
Plessel, et al., "$m_3G$ Cap Hypermethylation of U1 Small Nuclear Ribonucleoprotein (snRNP) In Vitro: Evidence that the U1 Small Nuclear RNA-(Guanosine-N2)-Methyltransferase is a Non-snRNP Cytoplasmic Protein that Requires a Binding Site on the Sm Core Domain," *Mol Cell Biol*. vol. 14, pp. 4160-4172, 1994.
Raker, et al., "The snRNP Core Assembly Pathway: Identification of Stable Core Protein Heteromeric Complexes and an snRNP Subcore Particle In Vitro," *EMBO Journal*, vol. 15, pp. 2256-2269, 1996.
Raker, et al., "Spliceosomal U snRNP Core Assembly: Sm Proteins Assemble onto an Sm Site RNA Nonanucleotide in a Specific and Thermodynamically Stable Manner," Molecular and Cellular Biology, vol. 19, pp. 6554-6565, 1999.
Stark, et al., "Arrangement of RNA an Proteins in the Spliceosomal U1 Small Nuclear Ribonucleoprotein Particle," *Nature*, vol. 409, pp. 539-542, 2001.
Sumpter, et al., "In Vitro Reconstitution of U1 and U2 snRNPs from Isolated Proteins and snRNA," Molecular Biology Reports, vol. 16: 229-240, 1992.
Temsamani, et al., "The U2 Small Nuclear Ribonucleoprotein Particle Associates with Nuclear Factors in a Pre-mRNA Independent Reaction," *The Journal of Biological Chemistry*, vol. 266, pp. 20356-20362, 1991.
Wang et al., "A Cell System with Targeted Disruption of the SMN Gene," *The Journal of Biological Chemistry*, vol. 276, pp. 9599-9605, 2001.
Will et al., "Spliceosomal UsnRNP Biogenesis, Structure and Function," *Curr Opin Cell Biol*, vol. 13, pp. 290-301, 2001.
Yong, et al. "Sequence-Specific Interaction of U1 snRNA with the SMN Complex," *EMBO Journal*, vol. 21, pp. 1188-1196, 2002.
Yong, et al., "Why do Cells Need an Assembly Machine for RNA-Protein Complexes?" *Trends in Cell Biology*, vol. 15(5), pp. 226-232, 2004.

* cited by examiner

FIG. 4A
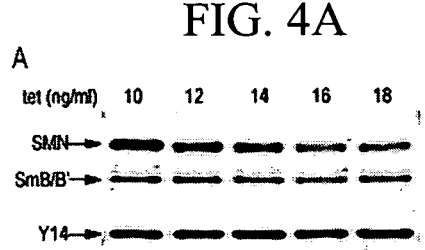
FIG. 4B
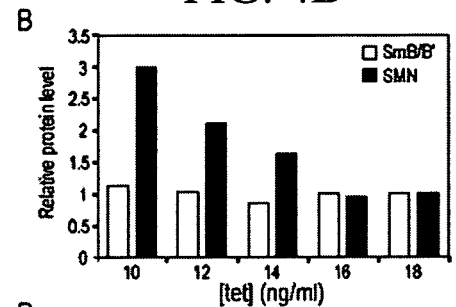
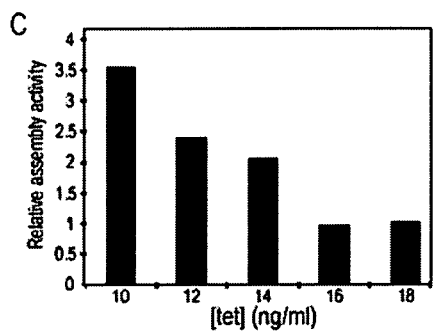
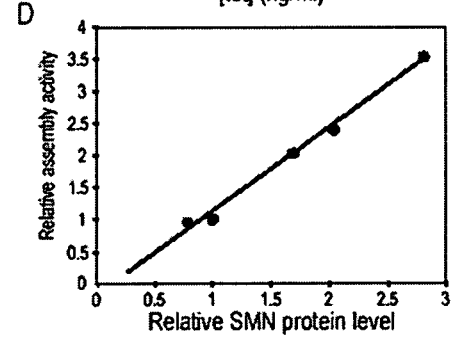
FIG. 4C
FIG. 4D 2,3-bis[(2-Hydroxyethyl)thio]-1,4-naphthoquinone Chelerythrine Chloride Gossypol

ASSAYS FOR DETECTING SMALL NUCLEAR RIBONUCLEOPROTEIN PARTICLE ASSEMBLY AND SURVIVAL OF MOTOR NEURONS ACTIVITY

CROSS-REFERENCE TO RELATED APPLICATIONS

The present application claims priority pursuant to 35 U.S.C. §119(e) to U.S. Provisional Application No. 60/660,634, filed Mar. 11, 2005, which is hereby incorporated by reference in its entirety herein.

BACKGROUND OF THE INVENTION

The process of pre-mRNA splicing is carried out by a macromolecular complex, the spliceosome, the major components of which are the U1, U2, U5 and U4/U6 small nuclear ribonucleoprotein particles (snRNPs) (Kambach, et al., 1999, Curr Opin Struct Biol 9: 222-230; Will and Luhrmann, 2001, Curr Opin Cell Biol 13: 290-301; Patel and Steitz, 2003, Nat Rev Mol Cell Biol 4, 960-970; Nilsen, 2003, Bioessays 25: 1147-1149). Each of the U snRNPs (except for U6) is composed of one snRNA molecule, a set of seven common proteins and several proteins that are specific to individual snRNAs (Will and Luhrmann, 2001, Curr Opin Cell Biol 13: 290-301; Luhrmann, 1990, Mol Biol Rep 14: 183-192; Luhrmann, et al., 1990, Biochim Biophys Acta 1087: 265-292). SnRNP biogenesis begins with the transcription of the snRNAs in the nucleus followed by their nuclear export to the cytoplasm, where the major assembly process of the snRNP takes place. The common proteins, called Sm proteins, B/B', D1, D2, D3, E, F, and G, are arranged into a stable heptameric ring, the Sm core, on a uridine-rich sequence motif (the Sm site) of the snRNAs (Branlant, et al., 1982, Embo J. 1: 1259-1265; Kambach, et al., 1999, Cell 96: 375-387; Stark, et al., 2001, Nature 409: 539-542; Achsel, et al., 2001, Proc Natl Acad Sci USA 98: 3685-3689). The assembly of Sm cores is required for the subsequent modification of the 7-methyl guanosine cap of snRNAs into a 2,2,7-trimethyl guanosine cap as well as for the stability and function of the snRNPs (Mattaj, 1986, Cell 46: 905-911; Plessel, et al., 1994, Mol Cell Biol. 14: 4160-4172). Properly assembled and modified snRNPs are then imported into the nucleus, where additional snRNP-specific proteins associate to form fully functional snRNPs (Will and Luhrmann, 2001, Curr Opin Cell Biol 13: 290-301; Mattaj, 1986, Cell 46: 905-911; Fischer and Luhrmann, 1990, Science 249; 786-790; Fischer, et al., 1993, Embo J. 12: 573-583; Hamm, et al., 1990, Cell 62: 569-577; Mattaj, et al., 1993, Mol Biol Rep 18: 79-83).

Earlier studies have demonstrated that snRNP assembly readily occurs in vitro with purified total snRNP proteins (TPs) and snRNAs (Sumpter, et al., 1992, Mol Biol Rep 16: 229-240; Raker, et al., 1996, Embo J. 15: 2256-2269; Raker, et al., 1999, Mol Cell Biol 19: 6554-6565) in an ATP-independent manner and without requirement for non-snRNP proteins. However, reconstitution of snRNPs in extracts from *Xenopus laevis* eggs and mammalian cells requires ATP (Kleinschmidt, et al., 1989, Nucleic Acids Res 17: 4817-4828; Temsamani, et al., 1991, J. Biol Chem 266: 20356-20362; Meister, et al., 2001, Nat Cell Biol 3, 945-949; Meister and Fischer, 2002, Embo J. 21: 5853-5863; Pellizzoni, et al., 2002, Science 298: 1775-1779), suggesting that snRNP assembly might be regulated by additional factors in vivo. Studies on a macromolecular complex containing the survival of motor neurons (SMN) protein indicated that the SMN complex is required for snRNP assembly (Temsamani, et al., 1991, J. Biol Chem 266: 20356-20362; Meister, et al., 2001, Nat Cell Biol 3, 945-949; Meister and Fischer, 2002, Embo J. 21: 5853-5863; Pellizzoni, et al., 2002, Science 298: 1775-1779; Fischer, et al., 1997, Cell 90: 1023-1029; Pellizzoni, et al., 1998, Cell 9: 615-624; Buhler, et al., 1999, Hum Mol Genet 8: 2351-2357; Yong, et al., 2004, Trends Cell Biol 14: 226-232). Experiments in cell extracts and with purified SMN complexes demonstrate that the SMN complex mediates the assembly of Sm cores (Meister, et al., 2001, Nat Cell Biol 3, 945-949; Meister and Fischer, 2002, Embo J. 21: 5853-5863; Pellizzoni, et al., 2002, Science 298: 1775-1779). SMN is the protein product of the gene responsible for spinal muscular atrophy (SMA), a common and often fatal genetic disorder in which motor neurons in the spinal cord degenerate (Lefebvre, et al., 1995, Cell 80: 155-165; Cifuentes-Diaz, et al., 2002, Semin Pediatr Neurol 9: 145-150; Iannaccone, et al., 2004, Curr Neurol Neurosci Rep 4: 74-80; Crawford, et al., 1996, Neurobiol Dis 3: 97-110). Based on the age of onset and the severity of the disease, SMA is clinically classified into three types: the severe type I, the moderate type II and the mild type III. The severity of SMA clinical phenotypes is closely linked to the degree of reduction of SMN protein levels in SMA patient-derived cell lines (Lefebvre, et al., 1997, Nat Genet 16: 265-269; Coovert, et al., 1997, Hum Mol Genet 6: 1205-1214).

Depletion experiments demonstrated that the SMN complex is required for snRNP assembly, but what happens in patients' cells, where the amount of the protein is reduced to varying degrees, has not been determined. Current methods of monitoring snRNP assembly are not suitable for quantitative analysis.

In addition, snRNP assembly is an excellent model for additional interactions between an RNA binding protein and RNA (RNA binding protein-RNA)U. Where the amount of the RNA binding protein is reduced to varying degrees, or activity is otherwise impaired or inhibited, pathogenesis ensues. However, current methods of monitoring RNA binding protein-RNA interaction and RNA binding protein assembly are not suitable for quantitative analysis.

There exists a long felt need to develop rapid, accurate and automatable assays to analyze snRNP assembly to determine the effect that SMA, as well as other diseases and conditions, have on the initiation of transcription. In addition, there exists a long felt need to develop rapid, accurate and automatable assays to analyze RNA binding protein-RNA interactions and the effect that the activation or inhibition of these interactions has on disease states. The present invention meets this need.

BRIEF SUMMARY OF THE INVENTION

The present invention encompasses an assay to detect an RNA binding protein specifically binding to an RNA, the assay comprising, transcribing a nucleic acid molecule in vitro in the presence of a first label to generate a labeled RNA molecule, contacting said labeled RNA molecule with a cellular extract and adenosine triphosphate (ATP), thereby forming an RNA binding protein-RNA complex, contacting said complex with a first antibody that specifically binds said RNA binding protein protein, contacting said first antibody with a detectable second antibody that specifically binds said first antibody, and detecting said second antibody, thereby detecting an RNA binding protein specifically binding to an RNA.

In one aspect of the present invention, the first label is a non-radioactive label.

In another aspect of the present invention, the non-radioactive label is biotin.

In yet another aspect of the present invention, the first label binds to a substrate.

In still another aspect of the present invention, the substrate is a multi-well plate.

In still another aspect of the present invention, the multi-well plate comprises a compound that binds said first label, wherein said compound is selected from the group consisting of avidin and streptavidin.

In yet another aspect of the present invention, the detectable second antibody comprises a non-radioactive tag.

In one aspect of the present invention, the non-radioactive tag is horseradish peroxidase.

In an aspect of the present invention, detecting said second antibody comprises detecting luminescence.

The present invention encompasses a kit for detecting an RNA binding protein specifically binding to an RNA, said kit comprising biotin-UTP, a first antibody that specifically binds an RNA binding protein, an detectable antibody that specifically binds said first antibody, and an instructional material for the use thereof.

The present invention comprises an assay to detect the activity of an RNA binding protein, the assay comprising, transcribing a nucleic acid molecule in vitro in the presence of a first label to generate a labeled RNA molecule, contacting said labeled RNA molecule with a cellular extract and adenosine triphosphate (ATP), thereby forming an RNA binding protein-labeled RNA molecule complex, contacting said complex with a first antibody that specifically binds said RNA binding protein, contacting said first antibody with a detectable second antibody that specifically binds said first antibody, and detecting said second antibody, thereby detecting activity of said RNA binding protein.

In one aspect of the present invention, the first label is a non-radioactive label.

In another aspect of the present invention, the non-radioactive label is biotin.

In yet another aspect of the present invention, the first label binds to a substrate.

In still another aspect of the present invention, the substrate is a multi-well plate.

In still another aspect of the present invention, the multi-well plate comprises a compound that binds said first label, wherein said compound is selected from the group consisting of avidin and streptavidin.

In yet another aspect of the present invention, the detectable second antibody comprises a non-radioactive tag.

In one aspect of the present invention, the non-radioactive tag is horseradish peroxidase.

In an aspect of the present invention, detecting said second antibody comprises detecting luminescence.

The present invention comprises a kit for detecting RNA binding protein activity, said kit comprising biotin-UTP, a first antibody that specifically binds an RNA binding protein, an detectable antibody that specifically binds said first antibody, and an instructional material for the use thereof.

The present invention also comprises a method of determining the amount of RNA binding protein in a cell, the method comprising detecting the level of RNA binding protein-RNA complex formation in a cell, wherein a lower level of RNA binding protein-RNA complex formation indicates a lower amount of RNA binding protein in a cell, further wherein a higher level of RNA binding protein-RNA complex formation indicates a higher amount of RNA binding protein in a cell.

The present invention comprises a method of identifying a compound that increases the level of RNA binding protein activity in a cell, the method comprising contacting a cell with a test compound and comparing the level of RNA binding protein-RNA complex formation in the cell with the level of RNA binding protein-RNA complex formation in an otherwise identical cell not contacted with the test compound, wherein a higher level of RNA binding protein-RNA complex formation in the cell contacted with the test compound compared with the level of RNA binding protein-RNA complex formation in the otherwise identical cell not contacted with the test compound is an indication that the test compound increases the level of RNA binding protein-RNA complex formation in a cell, thereby identifying a compound that increases the level of RNA binding protein activity in a cell.

The present invention encompasses the compound identified by the method above.

The present invention comprises a method of identifying a compound that decreases the level of RNA binding protein activity in a cell, the method comprising contacting a cell with a test compound and comparing the level of RNA binding protein-RNA complex formation in the cell with the level of RNA binding protein-RNA complex formation in an otherwise identical cell not contacted with the test compound, wherein a lower level of RNA binding protein-RNA complex formation in the cell contacted with the test compound compared with the level of RNA binding protein-RNA complex formation in the otherwise identical cell not contacted with the test compound is an indication that the test compound decreases the level of RNA binding protein-RNA complex formation in a cell, thereby identifying a compound that decreases the level of RNA binding protein activity in a cell.

The present invention encompasses the compound identified by the method above.

The present invention comprises an assay to detect a small nuclear ribonucleoprotein particle (snRNP) assembly, the assay comprising, transcribing a nucleic acid molecule in vitro in the presence of a first label to generate a labeled RNA molecule, contacting a substrate with said labeled RNA molecule wherein said labeled RNA specifically binds to said substrate, contacting said labeled RNA molecule with a cellular extract and adenosine triphosphate (ATP), contacting said labeled RNA molecule with a first antibody that specifically binds an Sm protein, contacting said first antibody with a second antibody that specifically binds said first antibody, and detecting said second antibody, thereby detecting snRNP assembly.

In one aspect of the present invention, the first label is a non-radioactive label.

In another aspect of the present invention, the non-radioactive label is biotin.

In still another aspect of the present invention, the substrate comprises a compound selected from the group consisting of avidin and streptavidin.

In yet another aspect of the present invention, the second antibody comprises a label.

In one aspect of the present invention, the label is horseradish peroxidase.

In one aspect of the present invention, detecting said second antibody comprises detecting luminescence.

The present invention comprises a kit for detecting snRNP assembly, said kit comprising a UTP-biotin, ATP, a first antibody that specifically binds an Sm protein, a second labeled antibody that specifically binds said first antibody, and an instructional material for the use thereof.

The present invention comprises an assay to detect activity of the survival of motor neuron (SMN) complex, said assay comprising, transcribing a nucleic acid molecule in vitro in the presence of a first label to generate a labeled RNA molecule, contacting a substrate with said labeled RNA molecule wherein said labeled RNA specifically binds to said substrate, contacting said labeled RNA molecule with a cellular extract and adenosine triphosphate (ATP), contacting said labeled RNA molecule with a first antibody that specifically binds an Sm protein, contacting said first antibody with a second antibody that specifically binds said first antibody, and detecting said second antibody, thereby detecting activity of the SMN complex.

In one aspect of the present invention, the first label is a non-radioactive label.

In another aspect of the present invention, the non-radioactive label is biotin.

In still another aspect of the present invention, the substrate comprises a compound selected from the group consisting of avidin and streptavidin.

In yet another aspect of the present invention, the second antibody comprises a label.

In one aspect of the present invention, the label is horseradish peroxidase.

In one aspect of the present invention, detecting said second antibody comprises detecting luminescence.

The present invention comprises a kit for detecting activity of the survival of motor neuron (SMN) complex, said kit comprising a UTP-biotin, ATP, a first antibody that specifically binds an Sm protein, a second labeled antibody that specifically binds said first antibody, and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A is an immunoblot depicting [$^{32}$P]UTP-labeled U1, U1 Sm, U1A3, U4, U4 Sm, U5 or U5 Sm snRNA mixed with HeLa cytoplasmic extracts containing total proteins (+lanes) or with buffer only (−lanes) for in vitro assembly of Sm cores. The brackets on the right indicate the assembled Sm cores and the free RNAs. FIG. 1B depicts the same reaction mixture depicted in FIG. 1A immunoprecipitated by Y12 bound to Protein A Sepharose beads. The RNAs that migrate at different positions on the gel are indicated on the right. FIG. 1C depicts similar assembly reactions as in FIG. 1A using biotin-UTP instead of [$^{32}$P]UTP and using either HeLa cytoplasmic extracts (+lanes) or buffer (−lanes).

FIG. 3, comprising FIG. 3A depicts in vitro assembly reactions performed using standard conditions except varying one of the following parameters: Sm core assembly on U4 (FIG. 3A through FIG. 3D) and U4 Sm (FIG. 3B through FIG. 3D) was examined by the magnetic beads assay and graphed against ATP or AMP-PNP concentration (FIG. 3A), the snRNA concentration (FIG. 3B), the amount of HeLa cytoplasmic extracts (FIG. 3C) or the assembly reaction time (FIG. 3D). Error bars represent standard deviations from 2 independent experiments.

FIG. 4, comprising FIGS. 4A through 4D, is a series of images depicting the correlation between reduced snRNP assembly with decreased SMN protein level in cell extracts. FIG. 4A depicts cytoplasmic extracts from cells cultured at 10, 12, 14, 16 or 18 ng/ml tet, respectively. FIG. 4B is a histogram depicting the intensity of each protein band depicted in FIG. 4A. FIG. 4C is an image depicting snRNP assembly capacities of the same extracts depicted in FIG. 4A. FIG. 4D is an image depicting the relative assembly activity at each tet concentration depicted in FIG. 4C plotted on the y-axis against the corresponding relative SMN protein level as in FIG. 4B on the x-axis.

FIG. 5, comprising FIG. 5A depicts total RNAs from labeled cells cultured at 10 or 18 ng/ml tet, respectively, and U RNAs isolated by immunoprecipitation. FIG. 5B is an image depicting the level of snRNPs in vivo at steady state in cells cultured at 10 or 18 ng/ml tet, respectively.

FIGS. 6A through 6C, is a series of images depicting that cells of SMA patients are deficient in snRNP assembly capacity. FIG. 6A depicts cytoplasmic extracts from lymphoblast cell lines established from a SMA type I patient (GM10684) and the other from an age- and gender-matched individual (GM12497) as a control. FIG. 6B depicts the intensity of each of the protein bands in FIG. 6A. FIG. 6C depicts cytoplasmic extracts from SMA patient fibroblast cell lines assayed by the magnetic beads assay.

FIG. 8, comprising FIG. 8A is an image depicting an assay to quantify SMN complex activity during snRNP assembly in the presence of a control compound, DMSO (dimethylsulfoxide). FIG. 8B is an image depicting an assay to quantify SMN complex activity during snRNP assembly in the presence of a test compounds. Circled data points indicate that the compound is an inhibitor of SMN activity and/or snRNP assembly.

FIG. 9 depicts the inhibitory activity of 22 screened compounds that inhibited SMN activity relative to the control, DMSO.

FIG. 10, comprising FIG. 10 also depicts the chemical structures of six of the identified inhibitors.

DETAILED DESCRIPTION OF THE INVENTION

Figure 1A:
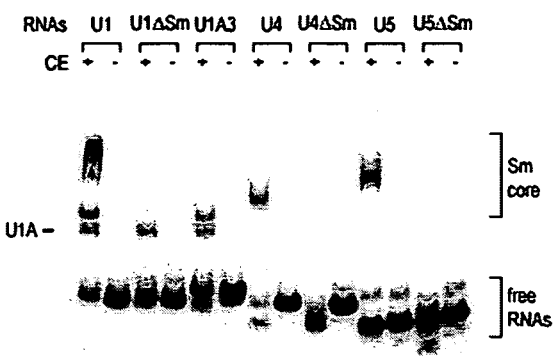
FIGS. 1A through 1C, is a series of images depicting the analysis of in vitro assembled snRNPs by mobility gel-shift assay and by a magnetic beads assay.

The present invention includes an assay and related methods to investigate and illuminate the molecular level functioning of RNA-binding proteins and their target RNA molecules. That is, the present invention includes assays and methods for determining the biochemical interaction between an RNA and an RNA-binding protein that binds the RNA. Thus, the methods of the present invention provide methods for identifying novel nucleic acid-protein interactions. Further, using the methods of the present invention, one of skill in the art can identify compounds that inhibit a reaction between an RNA and an RNA-binding protein. In addition, using the methods of the present invention, one of skill in the art can identify a compound that accelerates or otherwise facilitates the interaction between an RNA and an RNA-binding protein, thereby increasing the rate or frequency of reaction between the two molecules and any ancillary molecules involved in the binding reaction. Therefore, using the methods of the present invention, one of skill in the art can identify novel compounds useful for the treatment of diseases caused by insufficient or accelerated binding between an RNA and an RNA binding protein. Such diseases include, but are not limited to, SMA, described elsewhere herein, Fragile X Syndrome, and myotonic dystrophy. Fragile X syndrome is caused by deficiencies in Fragile X mental retardation protein (FMR1), an RNA-binding protein and the gene product characteristic of the disease. Myotonic dystrophy is neuromuscular disease caused by the binding of the muscleblind protein (Mbn1) to expanded CUG repeats in mRNAs.

The present invention further encompasses an assay to assess the relationship between the amount of SMN and the activity of Sm core assembly in cells and to facilitate further studies on the mechanism of SMN complex function. The assay disclosed in the present invention is a sensitive and quantitative assay for snRNP assembly. The assay of the present invention is also amenable to automation and therefore useful in high-throughput screening. The assay is based on the rapid isolation of high salt- and heparin-resistant Sm cores formed on biotin-labeled snRNAs with anti-Sm antibodies. The amount of snRNPs assembled in the reaction is then determined by luminescence detection of the biotin molecules on the snRNAs. As disclosed herein, the extent of assembly is directly dependent on the amount of the SMN complex in the cell extract, and extracts of cells from SMA patients have a lower capacity for snRNP assembly, proportional to the reduction of SMN protein in these cells. In vivo pulse labeling experiments disclosed herein demonstrate that the rate of biogenesis of the major snRNPs is strongly reduced in cells with low SMN. The data disclosed herein demonstrate that SMA can be the result of a deficiency in a specific biochemical activity in SMA patients and provide a powerful method for studying the activity of the SMN complex. However, the present invention is not limited to the use in studying SMA, but rather encompasses methods, assays and kits for detecting altered RNA-RNA binding protein interactions in a variety of cell types and disease states. RNA binding proteins and the RNAs they bind that are encompassed in the present invention include, but art not limited to, hnRNP proteins that interact with pre-mRNA and mRNA (e.g., hnRNP A1 interacting with Ad2 pre-mRNA), SMN complex components, such as SMN, Gemin3 and Gemin5, that interact with spliceosomal U snRNAs and snoRNA (small nucleolar RNA); FMR1 protein that interacts with mRNAs; and Argonaute2 (Ago2) protein that interacts with microRNAs (mRNAs) and siRNAs.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

By the term "applicator" as the term is used herein, is meant any device including, but not limited to, a hypodermic syringe, a pipette, an intravenous infusion, topical cream and the like, for administering Gemin2 inhibitor, such as a chemical compound, an antibody, a siRNA, a nucleic acid, protein, and/or composition of the invention to a mammal.

A "cellular extract" as used herein refers to a component of a cell including, but not limited to, a component from the nucleus, a component from the cytoplasm, a component from the membrane, a component from a vacuole, a component from an organelle, a cell fraction, a nuclear fraction, a membrane fraction, an organelle fraction, and the like.

As used herein, an "instructional material" includes a publication, a recording, a diagram, or any other medium of expression, which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container, which contains the nucleic acid, peptide, chemical compound and/or composition of the invention or be shipped together with a container, which contains the nucleic acid, peptide, chemical composition, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

"Constitutive" expression is a state in which a gene product is produced in a living cell under most or all physiological conditions of the cell.

"Inducible" expression is a state in which a gene product is produced in a living cell in response to the presence of a signal in the cell.

A "recombinant polypeptide" is one, which is produced upon expression of a recombinant polynucleotide.

A "label" refers to a compound that can be conjugated to an antibody, polypeptide, or nucleic acid that produces a detectable signal. A label, as used herein, can comprise a tag polypeptide, an isotope, a biotin molecule, an avidin molecule, a streptavidin molecule, a fluorescein molecule, and the like. A label can be detected either by the emission of a detectable signal or by a chemical reaction with another compound.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "portion" of a polynucleotide means at least at least about fifteen to about fifty sequential nucleotide residues of the polynucleotide. It is understood that a portion of a polynucleotide may include every nucleotide residue of the polynucleotide.

By the term "specifically binds," as used herein, is meant an antibody which recognizes and binds an antigen, but does not substantially recognize or bind other molecules in a sample.

I. Assays

A. Assays for Detecting snRNP Assembly

The present invention includes an assay for detecting the assembly of RNA binding proteins with RNA, including the assembly of snRNPs in a cell or organism and an assay for detecting the activity of RNA binding proteins and a conjugate RNA, including the formation of the SMN complex. This is because, as demonstrated by the data disclosed herein, the assay of the present invention can be used to determine the extent of biochemical dysfunction in a patient and develop a prognosis or course of therapy for the treatment of a disease. Additionally, sequence-specific RNA binding proteins are of major importance both for normal cellular control and in disease states such as cancer and specific genetic diseases disclosed elsewhere herein. These complexes are often short-lived and in low abundance, but such complexes are important regulatory proteins that are valuable drug targets. Thus, due to the short-lived nature of such complexes, robust, sensitive and accurate assays are required to identify such interactions.

Thus, the assay of the present invention is useful in determining the function and identity of specific members RNA binding protein-RNA complexes. As a non-limiting example, the present assay is useful in identifying the components of the snRNP complex, such as the Sm proteins (B/B', D1, D2, D3, E, F and G), and the spliceosome components, such as U1, U2, U5 and U4/U6, and SMN complex activity. The assay of the present invention is also useful in determining the function of specific members of other RNA complexes, especially the interaction of RNA binding proteins and RNA.

The present invention also includes a method for identifying a compound that inhibits or otherwise impairs the formation of an RNA binding protein-RNA complex. Examples of such complexes include the snRNP complex and the activity of the SMN complex. Such compounds are useful in the treatment of proliferative diseases in which the proliferative capacities of a cell need to be retarded in order to treat the disease. Proliferative diseases encompassed in the present invention include, but are not limited to, neoplasias, such a multiple myeloma, melanoma, lymphoma, solid tumors, and other cancers well known in the art. The present invention further encompasses non-cancerous proliferative diseases, such as psoriasis and other proliferative skin diseases.

A compound that impairs the formation of the RNA binding protein-RNA complex, such as the snRNP complex and the activity of the SMN complex, is useful in retarding the growth of an organism that requires RNA binding protein-RNA formation for cell growth and cell function. Therefore, as disclosed herein, impairing the formation of the such complexes and impairing the activity of such complexes can be useful as an anti-infective, similar to compounds such as streptomycin that impair protein synthesis, an anti-cancer treatment, such as taxol, which impairs microtubule formation, and the like. Thus, the present invention comprises methods for identifying compounds and compounds that can impair the formation of an RNA binding protein-RNA complex. Examples of such complexes include, but are not limited to, the snRNP complex and the activity of the SMN complex.

The present invention also includes a method for identifying a compound that increases the formation of an RNA binding protein-RNA complex, for example, the snRNP complex, and for assessing the activity of the SMN complex. Compounds that increase the activity of the SMN complex or increase the assembly of the snRNP complex are useful in the treatment of diseases in which such complexes are impaired, including, but not limited to, SMA. That is, as disclosed by the data herein, low levels of SMN protein or low levels of SMN protein activity results in, inter alia, impairment of snRNP complex formation, leading the pathogenic phenotype of SMA. Thus, as disclosed herein, a compound that increases the activity of the SMN complex or the assembly of the snRNP complex is a valuable therapeutic for the treatment of diseases such as SMA. In addition, a compound that increases the activity or formation of an RNA binding protein-RNA complex is valuable for treating diseases in which the formation of such complexes is impaired.

The assay of the present invention can further be used to determine the molecular mechanism of the pathogenesis of a disease. This is because, as disclosed elsewhere herein, a reduction in the level of SMN in a cell results in a reduced capacity for snRNP assembly, resulting in a decrease in biochemical activity. Such decreases in biochemical activity can result in decreased cell growth and cell death, phenomena characteristic of cells with reduced levels of SMN, the causative factor in SMA. Thus, the assay of the present invention can be used to assess the molecular mechanism of a disease, thus elucidating the pathological phenotype and illuminating methods of treatment. Such diseases include, but art not limited to, SMA, Fragile X Syndrome, and myotonic dystrophy.

The assay of the present invention further provides an improvement over other assays for the detection of RNA binding protein-RNA complex assembly because the assay disclosed herein does not require the use of radio-labeled nucleic acids and does not require the lengthy process of gel electrophoreses. Therefore, the assay of the present invention is less hazardous and faster than other assays, making in amenable to high-throughput screening techniques. Further, the assay disclosed herein does not require any additional separation steps, and therefore can be performed in one substrate, such as a multi-well plate, thereby simplifying and increasing the speed of the assay.

The assay of the present invention comprises transcribing a nucleic acid using in vitro techniques well known in the art. In vitro transcription requires a purified linear DNA template containing a promoter, ribonucleotide triphosphates, a buffer system that includes DTT and magnesium ions, and an appropriate phage RNA polymerase. The exact conditions used in the transcription reaction depend on the amount of RNA needed for a specific application, and are readily determinable by those of skill in the art. The common RNA polymerases used in in vitro transcription reactions are SP6, T7 and T3 polymerases. These RNA polymerases are DNA template-dependent with distinct and specific promoter sequence requirements. The promoter consensus sequences for each of the phage RNA polymerases are known in the art. Further, such promoter sequences are included on most commercially available plasmids. Kits for in vitro transcription of a nucleic acid are widely available, from, for example, Ambion (Woodward, Tex.).

The assay of the present invention comprises labeling the RNA transcribed with a first label. As demonstrated by the data disclosed herein, the first label can be a non-radioactive label, such as biotin, or a radioactive label, such as $^{32}P$. Non-radioactive labels are well known in the art. Preferably, the non-radioactive label used in the methods of the present invention is a non-radioactive label that specifically binds another molecule. Even more preferably, the non-radioactive label is biotin or another non-radioactive label known in the art.

The present invention further comprises the use of additional non-radioactive labels and/or tags that can be incorporated or otherwise bound or conjugated to an RNA molecule to allow capture or detection of the RNA in the assays of the present invention. Such additional non-radioactive tags included, but are not limited to, digoxygen (and the corresponding antibody that specifically binds digoxygen, Roche, Indianapolis, Ind.), dinitrophenol (DNP), nucleotide derivatives, and the like.

The first label is incorporated into the RNA through a ribonucleotide triphosphate conjugated to a first label. Such labeled ribonucleotide triphosphates are known in the art and include digoxigenin-labeled, biotin-labeled ribonucleotide triphosphate and $^{32}P$ labeled ribonucleotide triphosphates. Preferably the non-radioactive labeled ribonucleotide triphosphate is biotin-labeled UTP.

In one embodiment of the present invention, the labeled RNA is aliquoted into or otherwise placed in contact with a substrate which comprises a compound that specifically binds to the labeled RNA. The substrate is preferably a multi-well plate, such as a 96-well plate, a 384-well plate, or preferably, a 1536-well plate, or other plates known in the art. Such plates are available commercially from, for example, Nunc (Rochester, N.Y.). However, as is apparent to the skilled artisan when equipped with the present disclosure and the methods set forth herein, any substrate useful for cellular assays will work with the assay of the present invention.

The substrate is coated or otherwise contacted with a compound that specifically binds the labeled RNA. As a non-limiting example, the substrate can be coated with avidin or streptavidin, such that it binds a biotin label incorporated into the labeled RNA. However, other such compounds that specifically bind a label are contemplated in the present invention and are disclosed elsewhere herein.

The labeled RNA molecule generated by in vitro transcription is then contacted with a cellular extract, such as a protein extract, a cytoplasmic extract, a nuclear extract, and the like, from a cell. The cellular extract is from a cell of interest, such as a cell from a proliferative disease, a cell from a patient with a disease or condition of interest, and the like. The cellular extract is produced using methods well known in the art and described elsewhere herein, such as, but not limited to, those described in Pellizzoni et al. (2002, Science 298: 1775-1779). Other methods of producing cellular extracts are well known in the art and are described in, for example, Sambrook et al. (2001, Molecular Cloning: A Laboratory Manual, Third Edition, Cold Spring Harbor Laboratory, New York), in Ausubel et al. (1997, Current Protocols in Molecular Biology, John Wiley & Sons, New York).

The labeled RNA molecule is also contacted with ATP to drive the assembly of the RNA binding protein-RNA complex. This is because, as demonstrated elsewhere herein, a non-hydrolysable ATP analog, AMP-PNP, does not permit the formation of an RNA binding protein-RNA complex, such as the snRNP complex.

The mixture of labeled RNA, cell extract and ATP in a substrate can then be contacted with a test compound to determine if that test compound inhibits or increases the formation of an RNA binding protein-RNA complex. That is, using the invention disclosed herein, one of skill in the art can identify a compound that accelerates the formation of an RNA binding protein-RNA complex or inhibits the formation of an RNA binding protein-RNA complex. Such compounds include, but are not limited to, hexachlorophene, bithionol, beta-lapachone, 2,3-bis[(2-Hydroxyehtyl)thio]-1,4-naphthoquinone, chelerythrine chloride, gossypol, the compounds identified elsewhere herein (e.g. FIG. 9), and other compounds known or to be discovered in the art identifiable by the assays and methods of the present invention.

In the methods of the present invention, the substrate, such as a 1536 well plate, or other substrate disclosed herein or known in the art, is then washed to remove any unbound RNA, unbound cellular extract, and expended ATP. As disclosed elsewhere herein, multiple washes are appropriate in order to remove any unbound nuclear or cellular components contacting the substrate.

The washed mixture of labeled RNA, any residual ATP and cellular extract is then contacted with an antibody that binds to an RNA-binding protein. As a non-limiting example, the mixture of labeled RNA, cell extract and ATP is then contacted with an antibody that specifically binds an Sm protein present in the snRNP assembly. Such antibodies are well known in the art and include the Y12 monoclonal antibody (Pisetsky et al., 1982, J. Immunol. 129: 1489-92), anti-argonaut2 antibody (eIF2C2 antibody 8C7) (Imgenix, San Diego, Calif.); anti Hnrnp A1 antibody (4B10) (Abcam, Cambridge, UK), poly A binding protein antibody (Immuquest, Cleveland, UK), FMR1 protein antibody (EF8) (Immuquest, Cleveland, UK), SMN, Gemin3 and Gemin5 complex antibodies (2B1, 12H12 and 10G11, respectively) (Santa Cruz Biotechnology, Santa Cruz, Calif.), and the like.

The skilled artisan would also appreciate, based on the disclosure provided herein, that an antibody that specifically binds an RNA binding protein can be produced using standard methods disclosed herein or well known to those of ordinary skill in the art (Harlow et al., 1988, Antibodies: A Laboratory Manual, Cold Spring Harbor, N.Y.). Thus, the present invention is not limited in any way to any particular antibody; instead, the invention includes any antibody that specifically binds with an RNA binding protein either known in the art and/or identified in the future.

The assay of the present invention further comprises contacting the mixture of labeled RNA, cellular extract, RNA binding protein antibody and ATP with a detectable second label that specifically binds the first label. Such labels are well known in the art and include, for example, streptavidin, avidin, radioactive labels, and the like. The second label further comprises a detectable tag, such as, but not limited to, horseradish peroxidase, FITC, Texas Red, fluorescein, and the like. The detectable tag facilitates the detection of the RNA binding protein-RNA complex in a cell. Preferably, the second label is an antibody with a detectable tag, such as horseradish peroxidase. The choice of antibody depends on the antibody that is specifically bound to the RNA binding protein. As an example, if a murine antibody is used as the primary antibody to specifically bind to an RNA binding protein, the secondary antibody can be a goat anti-mouse antibody, a horse anti-mouse antibody, a sheep anti-mouse antibody, and the like. Labeled secondary antibodies are well known in the art.

The detectable tag is then detected using methods well known in the art, including, but not limited to, chemiluminescence, microscopy, spectrophotometry, an automatic plate reader, autoradiography using X-ray film, and the like. A signal is detected from the RNA binding protein-RNA assembly, indicating the formation of the complex. Further, as disclosed elsewhere herein, the assay of the present invention allows quantitative analysis of the speed in which the RNA binding protein-RNA assembly forms, providing information regarding any dysfunction in RNA binding protein-RNA assembly.

The present invention further encompasses an assay for the detection of snRNP complex formation and the activity of the SMN complex. The assay of the present invention comprises transcribing a nucleic acid molecule in vitro in the presence of a first label to generate a labeled RNA molecule. The nucleic acid molecule is transcribed in vitro using the methods and compositions described elsewhere herein, including the use of in vitro transcription kits that are commercially available.

The labeled RNA is then contacted with a cellular extract, as described elsewhere herein. The labeled RNA is also contacted with ATP because, as disclosed elsewhere herein, ATP is required for the assays of the present invention.

The assay of the present invention further comprises contacting the labeled RNA with an antibody that specifically binds an Sm protein. Antibodies that binds an SM protein, or a component of the snRNP assembly are disclosed elsewhere herein, and include, but are not limited to, the Y-12 antibody.

The antibody of the present invention is preferably bound to a substrate, such as a magnetic bead, to facilitate the rapid immunoprecipitation of the snRNP complex. Conjugating an antibody to a magnetic bead is well known in the art, and usually comprises the use of *Staphylococcus* Protein A or Protein G in order to facilitate immobilization of an antibody. Further, magnetic beads are available commercially, for example, from Dynal Biotech (Brown Deer, Wis.).

The first antibody that specifically binds an Sm protein is then contacted with a second antibody that specifically binds the first antibody. Preferably, the antibody is labeled with a detectable compound, including, but not limited to an isotope, horseradish peroxidase, and other labels disclosed herein.

The assay further comprises detecting the label of the second antibody, thus detecting the formation of the snRNP complex and detecting SMN activity. Detection of the label is performed according to the methods disclosed elsewhere herein.

The assays of the present invention can also be modified using a hybridization reaction to detect an RNA. Briefly, a nucleic acid probe can be used to specifically bind an RNA in which an RNA binding protein-RNA complex, such as an snRNP complex, has formed. The invention encompasses probes and primers for detecting the expression, amount, or activity of an RNA binding protein-RNA complex. The skilled artisan, when equipped with the present disclosure and the data disclosed herein, will appreciate that probes are provided that are capable of specifically hybridizing to DNA or RNA of a gene of interest. For purposes of the present invention, probes are "capable of hybridizing" to DNA or RNA of a gene of interest if they hybridize to the gene under conditions of either high or moderate stringency, see Sambrook et al. (2001, Molecular Cloning: A Laboratory Manual, Third Edition, Cold Spring Harbor Laboratory, New York) but not significantly or detectably to an unrelated gene. Preferably, the probe hybridizes to suitable nucleotide sequences under high stringency conditions, such as hybridization in 5×SSPE, 1× Denhardt's solution, 0.1% SDS at 65° C., and at least one wash to remove unhybridized probe in the presence of 0.2×SSC, 1× Denhardt's solution, 0.1% SDS at 65° C. Except as otherwise provided herein, probe sequences are designed to allow hybridization to a gene of interest, but not to DNA or RNA sequences from other genes. The probes are used, for example, to hybridize to nucleic acid that is present in a biological sample, including, but not limited to, a cell from a patient. The hybridized probe is then detected, thereby indicating the presence of the desired cellular nucleic acid. The skilled artisan will recognize that the cellular nucleic acid can be subjected to an amplification procedure, such as polymerase chain reaction (PCR), prior to hybridization.

Nucleic acid probes of the present invention may be composed of either deoxyribonucleic acids (DNA), ribonucleic acids (RNA), nucleic acid analogues (e.g., peptide nucleic acids), or any combination thereof, and can be as few as about 12 nucleotides in length, usually about 14 to 18 nucleotides in length, and possibly as large as the entire sequence of a gene of interest. Selection of probe size is somewhat dependent upon the use of the probe, and is well within the skill of the art.

Suitable probes can be constructed and labeled using techniques that are well known in the art. Shorter probes of, for example, 12 bases can be generated synthetically and labeled with $^{32}P$ using T4 polynucleotide kinase. Longer probes of about 75 bases to less than 1.5 kb are preferably generated by, for example, PCR amplification in the presence of labeled precursors such as, but not limited to, $[\alpha^{32}P]$ dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells, see Sambrook et al., supra.

Probes can be labeled by a variety of markers, including for example, radioactive markers, fluorescent markers, enzymatic markers, and chromogenic markers. The use of $^{32}P$ is but one example for marking or labeling a particular probe.

II. Methods of Identifying a Useful Compound

The present invention includes a method of identifying a compound that increases the level of RNA binding protein activity in a cell. The method of the present invention comprises contacting a cell with a test compound and comparing the level of RNA binding protein-RNA complex formation in the cell with the level of RNA binding protein-RNA complex formation in an otherwise identical cell not contacted with the test compound. As demonstrated by the data disclosed herein, a higher level of RNA binding protein-RNA complex formation in the cell contacted with the test compound compared with the level of RNA binding protein-RNA complex formation in the otherwise identical cell not contacted with the test compound is an indication that the test compound increases the level of RNA binding protein-RNA complex formation in a cell. The compound of the present invention therefore increases the level of RNA binding protein activity in a cell. As an example that is disclosed elsewhere herein, the assays of the present invention can be used to determine the level of activity of the SMN protein.

A compound identified by the method of the present invention is useful in the treatment of various diseases, including SMA. This is because, as demonstrated by the data disclosed herein, low levels of SMN and/or decreased acitivity of SMN results in an impaired formation of the snRNP complex, resulting in, among other things, cell growth arrest and cell death. Therefore, the compound of the present invention is useful in reversing this phenotype of the SMA cell, and is therefore useful in treating SMA.

The present invention also includes a method of identifying a compound that decreases the level of RNA binding protein activity and/or RNA binding protein-RNA complex formation in a cell. The method of the present invention comprises contacting a cell with a test compound and comparing the level of RNA binding protein-RNA complex formation in the cell with the level of RNA binding protein-RNA complex formation in an otherwise identical cell not contacted with the test compound. As demonstrated by the data disclosed herein, a lower level of RNA binding protein-RNA complex formation in the cell contacted with the test compound compared with the level of RNA binding protein-RNA complex formation in the otherwise identical cell not contacted with the test compound is an indication that the test compound decreases the level of RNA binding protein-RNA complex formation in a cell. The compound of the present invention therefore decreases the level of RNA binding protein activity in a cell.

A compound that impairs the formation of the RNA binding protein-RNA complex and the activity of an RNA binding protein is useful in retarding the growth of an organism that requires RNA binding protein-RNA formation for cell growth and cell function. Therefore, a compound that impairs the formation of the RNA binding protein-RNA complex and the activity of the RNA binding protein can be useful in the treatment of proliferative diseases, such as, but not limited to, cancer, proliferative skin diseases, and the like.

III. Kits

The invention encompasses various kits relating to detecting RNA binding protein-RNA assembly in a mammal or a cell. Although exemplary kits are described below, the contents of other useful kits will be apparent to the skilled artisan in light of the present disclosure. Each of these kits is included within the invention. The kits of the present invention are useful, because, as disclosed elsewhere herein, such kits can be used to determine the extent of biochemical dysfunction in a patient and develop a prognosis or course of therapy for the treatment of a disease. Further, the kits of the present invention are useful in determining the function of specific members of the RNA binding protein-RNA complex and the spliceosome components, such as U1, U2, U5 and U4/U6. The kits of the present invention can also be used to identify compounds that inhibit or otherwise impair the formation of the RNA binding protein-RNA complex. Thus, in one aspect, the invention includes a kit for detecting the formation of an RNA binding protein-RNA complex in a cell or mammal. The kit can comprise a labeled ribonucleotide triphosphate, adenosine triphosphate, an antibody that specifically binds an RNA binding protein, and a detectable second label for detecting the formation of the RNA binding protein-RNA complex. As disclosed elsewhere herein, the second label can be radioactive or non-radioactive, but is preferably a non-radioactive label, such as horseradish peroxidase. The kit further comprises an instructional material for the use thereof to be used in accordance with the teachings provided herein. The kits and the assays of the present invention can be performed in any single or multi-well plate useful for such assays and kits. As an example, the assays and kits of the present invention can be used in a 96-well plate, a 384-well plate, a 1536 well plate, or any other such plates known in the art.

In one embodiment, the invention includes a kit for detecting the formation of an RNA binding protein-RNA complex in a cell or mammal. The kit can comprise a label for labeling a ribonucleotide triphosphate, adenosine triphosphate, an antibody that specifically binds an RNA binding protein, and a detectable second label for detecting the formation of the RNA binding protein-RNA complex. Preferably, the detectable second label in a horseradish peroxidase conjugated antibody. The kit further comprises an instructional material for the use thereof to be used in accordance with the teachings provided herein.

A kit of the present invention can also include a labeled ribonucleotide triphosphate, ATP, a first antibody that specifically binds an RNA binding protein, a second labeled antibody that specifically binds the first antibody, and an instructional material for the use of the kit. As disclosed elsewhere herein, the second label can be radioactive or non-radioactive, but is preferably a non-radioactive label. The kit further comprises an instructional material for the use thereof to be used in accordance with the teachings provided herein.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Cells from SMA Patients have a Detectably Lower Capacity for snRNP Formation

In Vitro Transcription of RNAs

Plasmids for in vitro transcription of snRNAs were generated as described (Mattaj, 1986, Cell 46: 905-911; Fischer and Luhrmann, 1990, Science 249; 786-790; Hamm, et al., 1990, Cell 62: 569-577; Jarmolowski, et al., 1993, Embo J. 12: 223-232). For radio-labeling of RNAs, in vitro transcription was carried out in the presence of [$^{32}$P]UTP as described in Yong, et al. (2002, Embo J 21: 1188-1196). Biotin-labeled RNAs were produced according to the manufacturer's protocol (Ambion, Woodward, Tex.) with the modification that 5 mM biotin-UTP (Roche, Indianapolis, Ind.) and 2.5 mM UTP were present. All of the labeled RNAs were purified by electrophoresis on 7 M urea/6% polyacrylamide gels, precipitated with ethanol, and resuspended in nuclease-free water. The concentrations of the biotin-labeled RNAs were determined by absorbance at 260 nm.

Cell Lines and Cell Culture Maintenance

The maintenance of the S5 cell line, which is a chicken DT40 cell line with targeted disruption of the SMN gene, is described in Wang and Dreyfuss, 2001, J. Biol Chem 276: 9599-9605). EBV-transformed lymphoblast cell lines derived from a 6 month old SMA type I patient (GM10684) and an age- and gender-matched individual with a syndrome unrelated to SMA as a control (GM12497) were obtained from Coriell Cell Repositories and maintained in RPMI 1640 medium (Gibco BRL, La Jolla, Calif.) containing 10% fetal bovine serum (HyClone, Logan, Utah) and 1% penicillin-streptomycin (Gibco BRL). Primary fibroblast cell lines from four SMA type I patients (GM00232, GM09677, GM03813 and GM03815), one heterozygous carrier (GM03814) and two apparently healthy controls (GM08333 and GM00498) were also obtained from Coriell Cell Repositories. These cells were maintained in minimum essential medium (Gibco BRL) containing 15% fetal bovine serum, 2 mM L-glutamine and 1% penicillin-streptomycin.

Preparation of Cytoplasmic Extracts from Cultured Cells

For each sample in the assays disclosed here, the same number (~4×10$^7$) of cells were harvested and washed twice with PBS. For the SMA fibroblast cell lines, cells used were at the early and the same passage stage. Cytoplasmic extracts competent for snRNP assembly were prepared as described in (Pellizzoni, et al., 2002, Science 298: 1775-1779). The protein concentrations of the various extracts were determined using the Bio-Rad protein assay (BIO RAD, Hercules, Calif.). All of the extracts were adjusted to the same final protein concentration (~15 µg/ml for extracts prepared from HeLa cells, S5 cells or SMA lymphoblastoid cells, and 3 µg/ml for extracts of SMA fibroblast cells) and were quickly frozen in liquid nitrogen and stored in aliquots at −80° C.

Assay for In Vitro Assembly of snRNPs

For in vitro Sm core assembly on $^{32}$P-labeled snRNAs in cytoplasmic extracts, the reactions were carried out at 30° C. for 1 hour using standard assembly reaction conditions (Pellizzoni, et al., 2002, Science 298: 1775-1779). Subsequently, half of the reaction mixtures were loaded onto native gels for electrophoretic mobility shift assays as described in (Pellizzoni, et al., 2002, Science 298: 1775-1779). The other half of the samples were immunoprecipitated with anti-Sm monoclonal antibody (Y12) (Lerner, et al., 1981, Proc Natl Acad Sci USA 78: 2737-2741), and the immunoprecipitated RNAs were isolated and analyzed by electrophoresis on 7 M urea/8% polyacrylamide gels.

For quantitative in vitro assembly assays on magnetic beads, cytoplasmic extracts were prepared and used for assembly on biotin-labeled snRNAs using the standard reconstitution conditions in 96-well plates. Following the reactions, Y12 antibodies immobilized onto the magnetizable Dynabeads Protein A (Dynal Biotech ASA, Oslo, Norway) in 100 µl of RSB-500 buffer (10 mM Tris/HCl pH 7.5, 500 mM NaCl, 2.5 mM MgCl$_2$) containing 2 mg/ml heparin, 0.1% NP-40, and 0.2 U/µl RNasin Plus RNase inhibitor (Promega, Madison, Wis.) were added to each well. Immunoprecipitations in the 96-well plates were carried out with gentle mixing at 750 rpm in a Thermomixer (Eppendorf, Germany) at 30° C. for 1 hour. The plates were subsequently transferred to a Kingfisher 96 magnetic particle processor (Thermo Labsystems, Vantaa, Finland) for automatic washing of the Dynabeads in each well with wash buffer (RSB-500, 0.1% NP-40) 5 times. After the last wash, beads bound to Y12 immunoprecipitated snRNPs were then resuspended in 120 µl of wash buffer containing 0.08 µg/ml horseradish peroxidase (HRP)-conjugated NeutrAvidin™ (Pierce, Rockford, Ill.). Following incubation at 30° C. for 1 hour with gentle mixing, the beads in each well were again washed five times with the Kingfisher 96 magnetic particle processor, and finally resuspended in 150 µl of SuperSignal ELISA Femto Substrate Working Solution (Pierce). The plates were transferred to a Wallac Victor2 multi-label plate reader (Perkin-Elmer, Wellesley, Mass.) for luminescence measurements at 495 nm. The resulting data were analyzed with Microsoft Excel.

Antibodies and Quantitative Immunoblotting

The anti-SMN (62E7), anti-Gemin2 (2E17), anti-Gemin3 (12H12), anti-Gemin4 (17D10), anti-Gemin5 (10G11), anti-Y14 (IF12) and anti-Sm (Y12) monoclonal antibodies have been described in Lerner, et al. (1981, Proc Natl Acad Sci USA 78: 2737-2741; Liu and Dreyfuss, 1996, Embo J. 15: 3555-3565; Liu, et al., 1997, Cell 90: 1013-1021; Charroux, et al., 1999 J. Cell Biol 147: 1181-1194; Charroux, et al., 2000, J. Cell Biol 148: 1177-1186; Gubitz, et al., 2002, J Biol Chem 277: 5631-5636; Kataoka, et al., 2000, Mol Cell 6: 673-682). The anti-mouse IgG secondary antibody labeled with IRDye 800 (Rockland, Gilbertsville, Pa.) was used at a dilution of 1:5000. Proteins from 20 µg of cytoplasmic extracts were separated on NuPAGE 4-12% Bis-Tris gels (Invitrogen, La Jolla, Calif.) and transferred to nitrocellulose membranes. Quantitative immunoblotting was performed per the manufacturer's instructions (Li-Cor, Lincoln, Nebr.). The membranes were scanned on an Odyssey infrared imaging system (Li-Cor), and the intensity of the protein bands was analyzed using the software provided by the manufacturer.

Pulse-label Measurements of the Rate of snRNP Biogenesis in Cells

Three days after chicken S5 cells were cultured in medium containing 10 or 18 ng/ml tetracycline, equal number of cells (1×10$^7$) were pulse-labeled with 25 Ci/ml [3$^H$]uridine (Amersham, Piscataway, N.J.) for one hour. Total RNAs were isolated from 10% of the labeled cells using TRIzol reagent (Invitrogen). Total cell extracts from the remaining cells were subjected to immunoprecipitation by Y12. The immunoprecipitated RNAs were isolated by proteinase K treatment followed by phenol-chloroform extraction and ethanol precipitation. Both total RNAs and Y12 immunoprecipitated RNAs were analyzed by electrophoresis on 7 M urea/8% polyacrylamide gels. Gels were then treated with Amplify solution (Amersham) and dried for autoradiography.

Quantitation of snRNPs in Cells

To determine the overall amount of snRNPs at steady state in cells, Y12 immunoprecipitations were performed using cell extracts from 1×10$^7$ S5 cells grown in the presence of either 10 or 18 ng/ml tetracycline. Y12 immunoprecipitated RNAs were isolated and radioactively labeled at the 3' end with [5'-$^{32}$P]pCp (Perkin-Elmer) and T4 RNA ligase (New England Biolabs, Beverly, Mass.). The labeled RNAs were analyzed by electrophoresis on 7 M urea/8% polyacrylamide gels and dried for autoradiography.

The results of the experiments presented in this Example are now described.

Development of a Quantitative Assay for snRNP Assembly

Assembled Sm cores comprised of seven-membered rings of Sm proteins, unlike the complexes of individual Sm proteins or a subset of Sm proteins with RNA, are extremely sturdy and resist dissociation even at high salt, heparin and urea (Raker, et al., 1996, Embo J. 15: 2256-2269; Hamm, et al., 1987, Embo J. 6: 3479-3485; Jarmolowski, et al., 1993, Embo J. 12: 223-232). This property provides the basis for a gel mobility shift assay to assess Sm core formation. In these assays, $^{32}$P-labeled snRNAs were incubated with purified Sm proteins, or a cell fraction containing Sm proteins such as extracts from HeLa cells or *Xenopus lavis* eggs, and the resistant Sm cores, resolved by electrophoresis from free RNAs, are visualized by their characteristic mobility shift after autoradiography of the native polyacrylamide gels (Kleinschmidt, et al., 1989, Nucleic Acids Res 17: 4817-4828; Temsamani, et al., 1991, J. Biol Chem 266: 20356-20362; Meister, et al., 2001, Nat Cell Biol 3, 945-949; Meister and Fischer, 2002, Embo J. 21: 5853-5863; Pellizzoni, et al., 2002, Science 298: 1775-1779). As demonstrated by the present gel-shift assay, Sm cores formed on Sm site-containing U1, U4 and U5 snRNAs when incubated in HeLa cytoplasmic extracts (FIG. 1A). Sm core assembly was strictly dependent on Sm proteins supplied by the extract (FIG. 1A) and on the presence of an Sm site on the snRNAs (FIG. 1A). Sm cores assembled only inefficiently on U1A3 (FIG. 1A), a U1 snRNA mutant that has three nucleotide substitutions in the loop of stem-loop 1 and is impaired in binding to the SMN complex Yong, et al., 2002, Embo J. 21: 1188-1196). However, due to the heterodisperse migration of large RNP complexes on native gels, the gel-shift assay is not a sensitive and objective method to accurately quantitate Sm core assembly. To further confirm the identity of the assembled complexes and to assess snRNP assembly more accurately, the assembly reaction mixtures were subjected to immunoprecipitations with the anti-Sm antibody (Y12) (Lerner, et al., 1981, Proc Natl Acad Sci USA 78: 2737-2741) under stringent conditions such that only snRNAs that have assembled high salt- and heparin-resistant Sm cores could be immunoprecipitated.

Figure 1B:

Following Y12 immunoprecipitation, $^{32}$P-labeled snRNAs on which Sm cores formed were eluted and analyzed by urea/polyacrylamide gel electrophoresis (Pellizzoni, et al., 2002, Science 298: 1775-1779; Hamm, et al., 1987, Embo J. 6: 3479-3485; Jarmolowski, et al., 1993, Embo J. 12: 223-232). Similar to the gel-shift assay, Sm cores assembled on the wild-type snRNAs, but not on the respective Sm mutants (FIG. 1B). A weak signal was detected for the U1A3 mutant, demonstrating a low level of Sm core formation on this mutant more clearly than on the gel-shift assay (FIG. 1B). The level of snRNP assembly can be estimated by autoradiography on a phosphorimager. While the $^{32}$P-labeled RNA bands obtained after immunoprecipitation with anti-Sm antibodies are more suitable to estimate assembled Sm cores, this approach, using radio-labeled RNAs, still has considerable shortcomings, such as the short half-life of the $^{32}$P-labeled RNAs and the laborious handling of the hazardous materials.

Figure 1C:
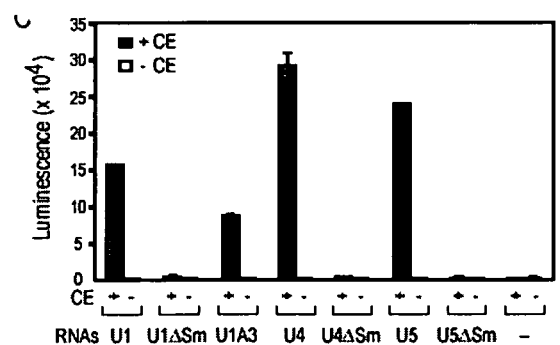
Figure 2:
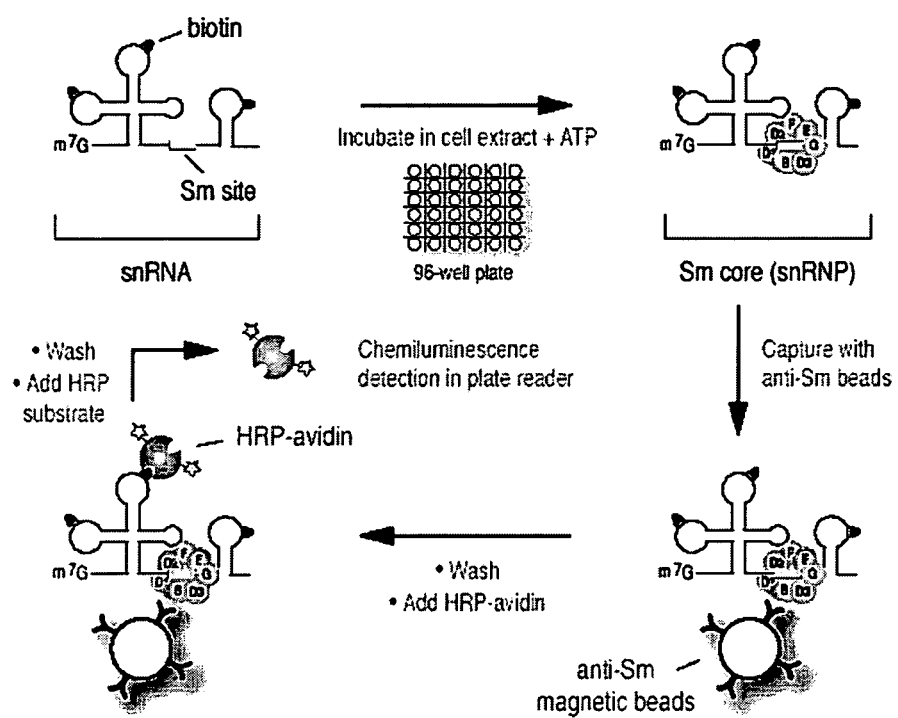
FIG. 2 is a schematic depiction of the magnetic beads assay procedure for the detection of in vitro assembled snRNPs.

To facilitate the study of the snRNP assembly process, an assay that allows a quantitative measurement of Sm core formation was developed (FIG. 2). Instead of labeling RNAs with [$^{32}$P]UTP, snRNAs were prepared by in vitro transcription in the presence of biotin-UTP. Following in vitro assembly reactions with the biotin-labeled RNAs, immunoprecipitations of the Sm cores were carried out under stringent conditions, including high salt (500 mM NaCl) and heparin (2 mg/ml). The immunoprecipitations were carried out with anti-Sm antibodies (Y12) immobilized on magnetic beads in a 96-well plate format, which allows automatic cycles of washing and mixing of the beads on a robotic manifold. Subsequently, horseradish peroxidase (HRP)-conjugated avidin, which binds tightly to biotin, was used to recognize the biotinylated RNAs in the Y12 immunoprecipitated Sm cores. This step also serves to amplify the signals for the luminescence measurement of the HRP activity on an automatic plate reader. The results obtained using this assay system (FIG. 1C) mirror those depicted in FIGS. 1A and 1B. The signal indicating the amount of assembly on U1, U4 and U5 is more than 100 fold above background (FIG. 1C). Readings on all Sm mutants were close to background, demonstrating the strict dependence of assembly on an Sm site. In this assay, the assembly of Sm cores on U1A3 is more significant than that was observed by the gel-shift assay or Y12 immunoprecipitation with $^{32}$P-labeled snRNAs. Since U1A3 binds to the SMN complex with lower affinity than wild-type U1 and Sm cores assemble on U1A3 with slower kinetics in vivo in *Xenopus* oocytes (Yong, et al., 2002, Embo J. 21: 1188-1196), the difference could be due to the higher concentration of U1A3 RNA and longer reaction time used in this assay. Notably, the experimental variation in independent experiments is typically less than 5% of the signal. The assay disclosed herein is more sensitive, much less labor-intensive than previous methods and amendable to high-throughput automation.

Figure 3A:
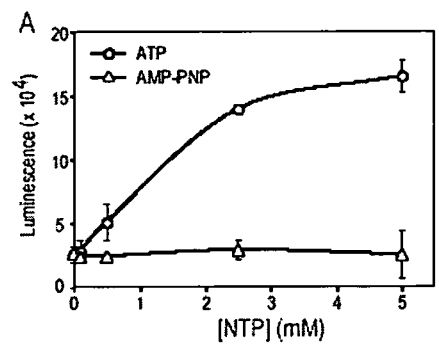
FIGS. 3A through 3D, is a series of images depicting that the in vitro assembly activity depends on ATP hydrolysis, the amount of the snRNAs, the amount of the cytoplasmic extracts and the reaction time.
Figure 3B:
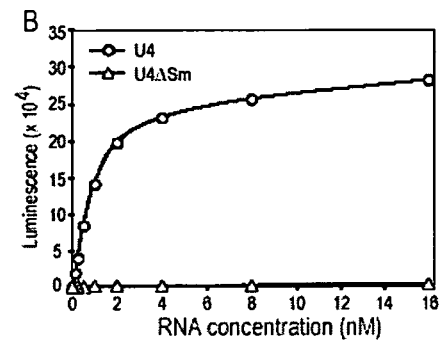
Figure 3C:
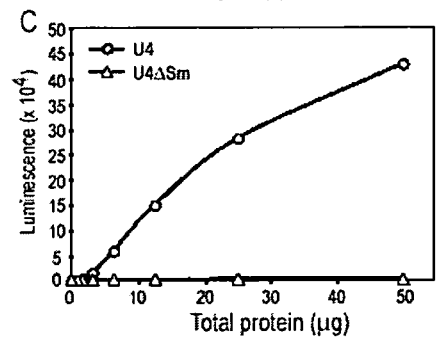
Figure 3D:
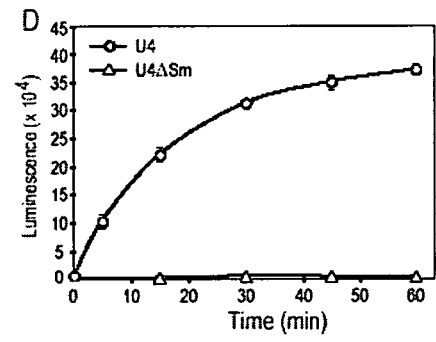

While the assembly of Sm cores from TPs is ATP-independent, energy is required for this process to occur in cell extracts (Kleinschmidt, et al., 1989, Nucleic Acids Res 17: 4817-4828; Temsamani, et al., 1991, J. Biol Chem 266: 20356-20362; Meister, et al., 2001, Nat Cell Biol 3, 945-949; Meister and Fischer, 2002, Embo J. 21: 5853-5863; Pellizzoni, et al., 2002, Science 298: 1775-1779). As demonstrated in FIG. 3A, Sm core assembly in extracts requires the addition of exogenous ATP, and does not occur with adenosine 5'-(β,γ-imido)triphosphate (AMP-PNP), a non-hydrolysable ATP analog, suggesting that ATP hydrolysis is required for assembly. To optimize the assay conditions, the effect of several parameters on the Sm core assembly were examined. Assembly on wild-type snRNA depends on RNA concentration, the amount of cytoplasmic extracts, and on the reaction time (FIGS. 3B-D). In contrast, Sm cores do not form on Sm mutant snRNAs even with excess RNAs, extracts and reaction time (FIGS. 3B-D). Similar profiles to those presented in FIG. 3 for U4 were obtained for U1 and U5. Since assembly activity corresponds linearly to the amount of extract (FIG. 3C) and plateaus at higher RNA concentration and longer reaction time (FIGS. 3B and 3D), the parameters used for our standard assembly reaction were: 5 nM biotinylated snRNA, cytoplasmic extracts containing 25 μg total proteins, and a reaction time of 60 minutes.

The SMN Protein Determines the Capacity for snRNP Assembly

It was previously demonstrated that the assembly of Sm cores is abolished when SMN complexes are depleted in vitro from cell extracts (Meister, et al., 2001, Nat Cell Biol 3, 945-949; Pellizzoni, et al., 2002, Science 298: 1775-1779). Since the assembly activity correlates with the amount of cytoplasmic extract (FIG. 3C), the amount of SMN in the extract that determines snRNP assembly capacity was investigated. To address this, SMN expression was reduced in HeLa cells by RNA interference, resulting in a drastic reduction in the assembly activity of the extracts prepared from these cells. However, RNAi cannot be regulated to obtain a specific reduction in the amount of the protein. Therefore, the S5 cell line, a cell line derived from the chicken DT40 cells, in which the endogenous SMN gene is disrupted by homologous recombination and SMN protein is exogenously expressed from a tetracycline (tet)-repressible (Tet-Off) promoter was used (Wang and Dreyfuss, 2001, J. Biol Chem 276: 9599-9605). This allows SMN expression to be tightly controlled to various levels by adjusting the concentration of tet in the culture media (Wang and Dreyfuss, 2001, J. Biol Chem 276: 9599-9605). Since the growth of S5 cells is arrested after 72 hours in the presence of 18 ng/ml tet and higher concentrations of tet lead to cell death (Wang and Dreyfuss, 2001, J. Biol Chem 276: 9599-9605), SMN expression was analyzed in S5 cells which were normally maintained in 10 ng/ml tet but were split into culture media containing 10, 12, 14, 16, or 18 ng/ml tet for three days. Equal numbers of cells (~4×10$^7$) were harvested for each of the respective tet concentrations and used to prepare cytoplasmic extracts. The expression level of Y14, a component of the exon-junction complex and unrelated to the snRNP assembly process, remained largely unchanged at various tet concentrations (FIG. 4A), and was therefore used as an internal control to determine the relative protein levels of SMN and Sm proteins B/B'. As demonstrated in FIG. 4B, the level of the SMN protein decreased with increasing tet concentration. Cells cultured at 18 ng/ml tet contained about 30% SMN compared to those at 10 ng/ml tet. Unlike the reduction of SMN, SmB/B' protein levels were not significantly changed.

A magnetic bead assay was employed to quantitate the assembly activity of these cell extracts. The capacity for assembly of Sm cores decreased with the reduction in SMN protein (FIG. 4C). When the relative assembly activity at each tet concentration was plotted against the corresponding relative SMN protein level, the data points were best fitted to a linear graph with a significant $R^2$ value ($R^2$=0.9911), indicating a direct correlation between the SMN protein level and assembly activity (FIG. 4D). These results demonstrate that SMN protein determines the capacity of Sm core assembly in cell extracts even as they contain similar, non-limiting amounts of Sm proteins.

Cells with Low SMN Accumulate snRNPs More Slowly

To determine if the reduced snRNP assembly capacity observed in extracts of cells with low SMN is reflected in vivo, the rate of snRNP biogenesis in cells was measured by pulse labeling. S5 cells cultured in the presence of either 10 ng/ml tet (normal SMN) or 18 ng/ml (low SMN) were compared. Pulse labeling of these cells demonstrated that the rate of accumulation of the major snRNAs and snRNPs, determined by a 1 hour [H$^3$]uridine incorporation into the major Sm-core-containing snRNAs, U1 and U2, was markedly reduced. The total amount of labeled U1 and U2 snRNAs, as well as other RNAs (e.g., 5S and tRNA) produced in the same time interval was also reduced. It is possible that low SMN cells also have reduced transcription rates or that RNAs, especially snRNAs, that are not assembled are rapidly degraded. The possibility that the rate of transcription is reduced is consistent with previous observations suggesting a role for the SMN complex in the formation of transcription factories. The data disclosed herein demonstrate that SMN is a critical factor in determining the rate of production of snRNPs in cells. The overall steady-state amount of the major snRNAs and snRNPs, determined by 3'-end labeling, was not significantly different in normal- and low-SMN cells. However, the low SMN cells have a much slower growth rate than normal SMN cells, possibly to allow these cells to accumulate the necessary amount of RNPs which now occurs at a slower rate.

Deficiency in snRNP Assembly in Cell Extract of SMA Patients

Figures 5A, 5B:
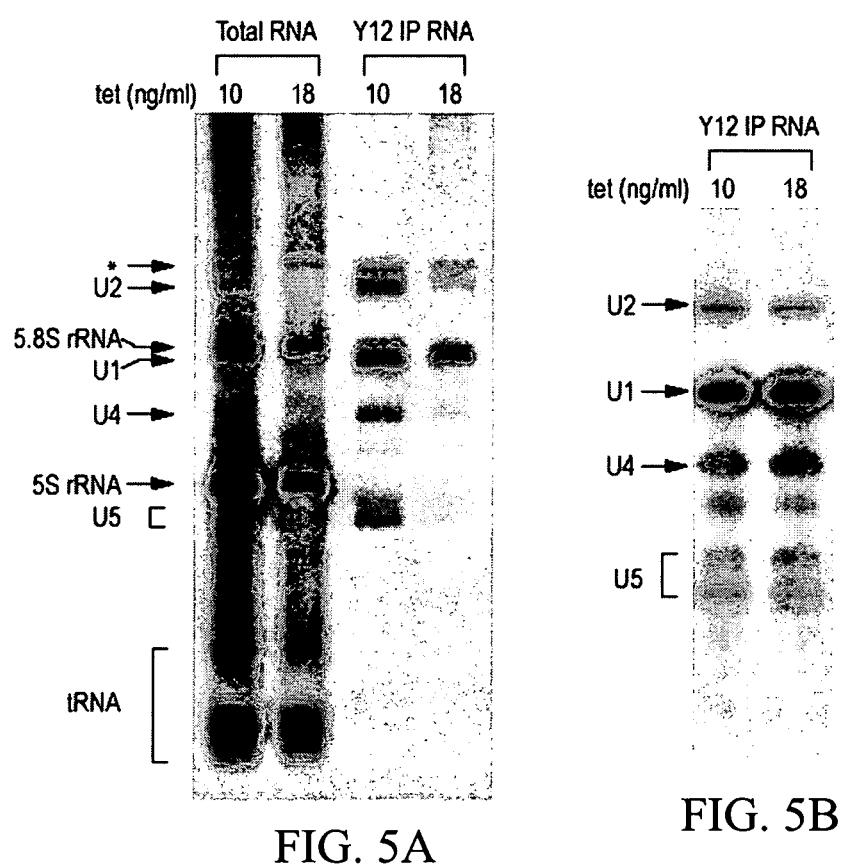
FIGS. 5A and 5B, is a series of images depicting that cells with low SMN maintain the level of snRNPs in vivo but accumulate snRNPs more slowly.
Figure 6:
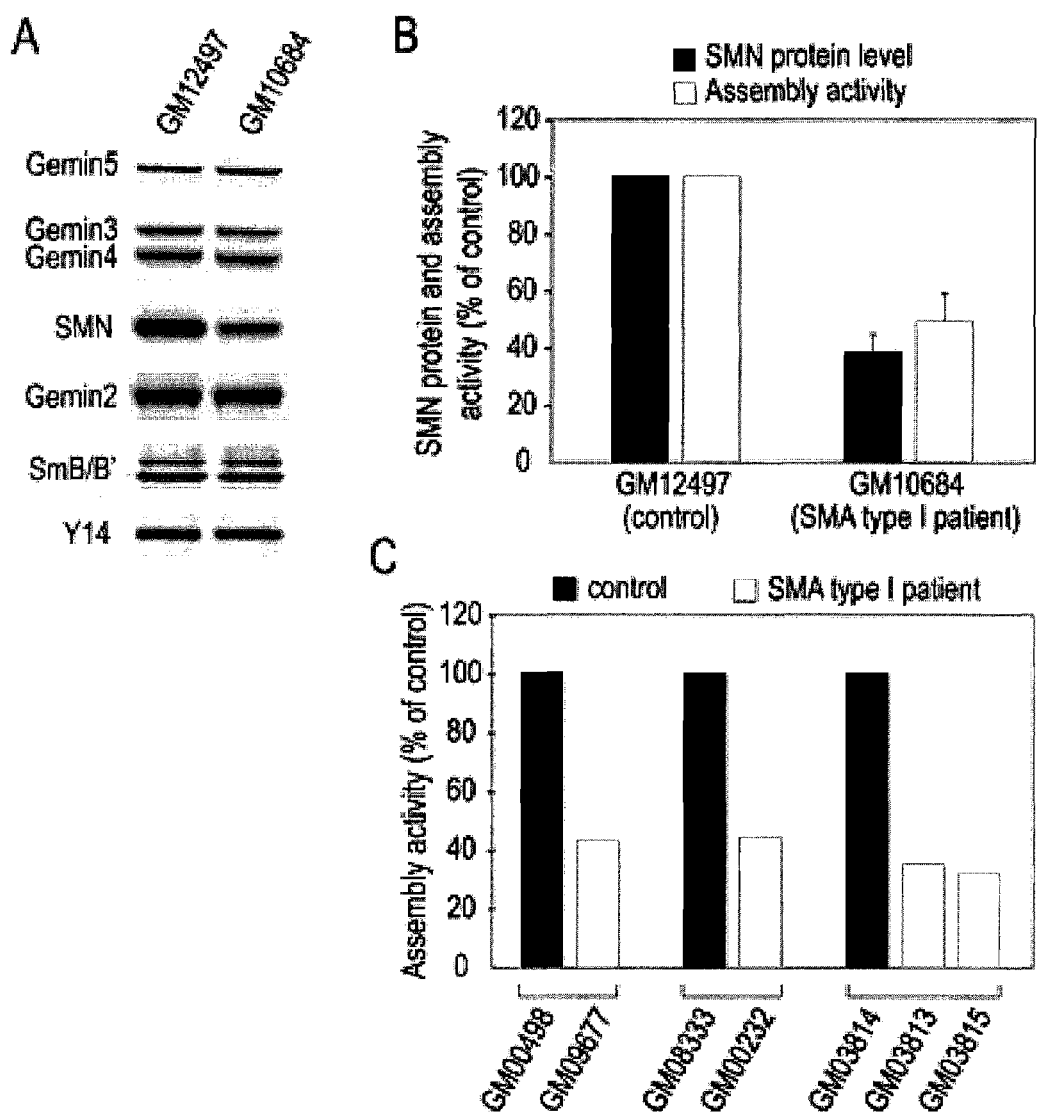
FIG. 6, comprising

In light of the findings described herein, specifically that SMN protein levels parallel the capacity of snRNP assembly in HeLa cells and in chicken S5 cells, cells from SMA patients were analyzed to determine if they were also deficient in snRNP assembly activity. A lymphoblastoid cell line derived from a type I SMA patient (GM10684) was examined using a similarly established cell line from an age- and gender-matched individual as a control (GM12497). Immunoblotting demonstrated that SMN in the patient cells was considerably reduced whereas the levels of Gemins2-5 and SmB/B' were similar to the control (FIG. 5A). Compared to the control, snRNP assembly activity of the patient cell extract was 48% of the control in three independent experiments. This assembly capacity correlates well with the SMN level, which was 38% of control (FIG. 5B), demonstrating a biochemical deficiency in cells of an SMA patient.

Several available sets of primary fibroblast cell lines derived from type I SMA patients, or heterozygous carriers, as well as unaffected individuals were also studied. The full-length SMN transcript levels and SMN protein levels in patient cells (GM09677, GM00232 and GM03813) were estimated to be about 40-50% of those of the respective controls (GM00498, GM08333 and GM03814) [40]. However, it was observed that the overall SMN protein levels in these fibroblast cells are very low and passage-dependent. Consequently, the assembly activities in these cells were considerably lower than those in the lymphoblastoid cells. The assembly assay revealed that extracts from the patient fibroblast cells had approximately 40% of the assembly activity compared to the corresponding controls (FIG. 5C), consistent with the degree of reduction of SMN protein in these patient cells. Interestingly, GM03815, described in the Coriell Cell Repository as the heterozygous carrier father of GM03813, also demonstrated a similar level of deficiency in snRNP assembly as GM03813 (FIG. 5C). Consistent with this, genetic linkage analysis indicated that GM03815 is, in fact, a male sibling of GM03813. Indeed, another affected son was listed in the family tree. These observations demonstrate that as a result of reduced levels of SMN protein expression, cells of SMA patients are deficient in the capacity of snRNP assembly in vitro, and demonstrate that the snRNP assembly assay can be used as a diagnostic tool for SMA.

Previous experiments have demonstrated that the SMN complex is required for snRNP assembly. Specifically, complete, or nearly complete, removal or inhibition of the SMN complex results in the inhibition of Sm core assembly in vitro (Meister, et al., 2001, Nat Cell Biol 3, 945-949; Pellizzoni, et al., 2002, Science 298: 1775-1779). Using an in vitro assay developed for the quantitative measurement of the Sm core assembly process in cell extracts, the data disclosed herein demonstrate that there is a linear correlation between the amount of SMN present in the cell extract and the amount of Sm cores that can be formed on specific RNA substrates, indicating that the amount of SMN determines the capacity for Sm core assembly. SMA results from a reduction in the amount of the full-length SMN protein. Studies on a collection of SMA patient cell lines revealed that SMN expression is more reduced in the severe form (type I) than the mild form (type III) of the disease, demonstrating a direct correlation between the degree of reduction of SMN protein levels in SMA patients and the severity of their clinical phenotype. However, an understanding of the molecular consequences of the reduced levels of SMN in patients' cells has been lacking. The present invention demonstrates that snRNP assembly is impaired in cells of SMA patients and provides the first direct evidence for a biochemical deficiency, namely, a reduced capacity to assemble Sm cores, in SMA patients. Due to a limited availability of SMA patients' cells, the present studies only focused on the severe type I SMA patients. However, the correlation disclosed herein is strong, exhibiting direct proportionality between the amount of the SMN protein and the assembly capacity in vitro. Consistent with the reduced activity observed in extracts of cells with low SMN, the rate of production of snRNPs is these cells is profoundly reduced. Although the overall amount of the major snRNPs in the same cells is not reduced, the strong deficiency in their rate of accumulation could be detrimental to cells in several ways. For dividing cells the slower rate of snRNP accumulation could cause a delay in cell cycle progression. This is indeed the case for S5 cells where the growth rate slows down proportionally to the reduction in SMN. In non-dividing cells, such as motor neurons, an unmet demand for a timely snRNP production at a particular point in the growth and development of the cell could have severe consequences to the cell. It could lead to a deficit in functions that depend on an adequate amount of the major snRNPs (e.g., a general decrease in pre-mRNA splicing or an altered processing pattern of pre-mRNA that are required by that cell), or to a deficit in a specific snRNP (e.g., a RNA of a lower abundance or one that has a lower affinity for the SMN complex). It is also possible that reduced amounts of SMN complex result in some loss of the regulation of Sm core assembly leading to loss of fidelity of Sm core assembly such that Sm cores assemble on RNAs that are not supposed to receive them. This could be harmful to cells as it may interfere with the normal function of these RNAs or cause them to aggregate. The experiments disclosed herein examined only the formation of the major snRNPs and it is therefore possible that the formation of minor snRNPs, motor neuron-specific snRNPs or other RNAs that require the SMN complex for RNP assembly, are strongly affected by the reduction in SMN.

High-Throughput, Non-Magnetic Assay

An assay was developed that can be used for high-throughput analysis of SMN activity, snRNP complex formation, RNA binding protein activity, RNA binding protein-RNA interaction, and the like. The present assay comprises labeling an RNA, in the case of an assay to measure Sm core activity, the RNA is snRNA. The RNA is preferably labeled with a non-radioactive tag, such as biotin-UTP. Cell extract and ATP are added to an avidin or streptavidin coated plate, preferably a 384 or 1536 well plate. The labeled RNA binds the plate through the interaction between biotin and avidin/streptavidin. The RNA binding proteins present in the cell extract bind their RNA target at sequence specific sites, forming a ribonucleoprotein complex in the multi-well plate substrate. The ribonucleoprotein complex is captured on the plate and the plate is washed one or more times. An anti RNA binding protein antibody is then added to the plate. The plate is again washed one or more times and an labeled antibody, such as an HRP labeled antibody, is added to the multi-well plate substrate. The plate is washed one or more times, and HRP substrate is added. Chemiluminescence generated by HRP is detected using a plate reader.

In one embodiment of the present invention, the assay is performed substantially as follows. The quantities of reagents can be scaled proportionally for use in different substrate formats (i.e. 96 well plates, 1536 well plates, and the like). Ten microliters of Reconstiution (RC) buffer (20 mM Hepes, 50 mM KCl, 5 mM $MgCl_2$, 5% glycerol, and 0.2 mM EDTA) containing 2.5 mM ATP, 0.25 mg/ml *Escherichia coli* tRNA, 0.2 U/ml RNasin RNase inhibitor and 10 nM biotinylated U4 snRNA was aliquoted into a 384-well neutravidin coated microplate. Five microliters of test compound dissolved in DMSO were added to each well of the plate. Five microliters of HeLa whole cell extract containing 8 µg of total protein was added to each well. The plate was centrifuged (5 minutes at 1000 rpm), and the assembly reactions were allowed to proceed for 1 hour at room temperature. The reaction mixtures were aspirated and 20 µl/well of Y12 antibody (diluted 1:1000 in RSB-500 (10 mM Tris/HCl, pH 7.5, 500 mM NaCl, 2.5 mM $MgCl_2$, and 0.1% Nonidet P-40 (NP-40)) containing 1 mg/ml BSA, 2 mg/ml heparin, and 1× Complete EDTA-free Protease Inhibitor Cocktail) was added. The plate was centrifuged for 5 minutes at 1000 rpm, and incubated for 1 hour at room temperature.

The plate was washed 10× with RSB-500 using an automated plate washer, followed by the addition of 20 ml/well of horseradish peroxidase-conjugated AffiniPure goat anti-mouse IgG+IgM (diluted 1:10,000 in RSB-500 containing 1 mg/ml BSA) for 1 hour at room temperature. The plate was centrifuged for 5 minutes at 1000 rpm. The plate was then washed 10× using an automated washer and 20 µl of Super-Signal ELISA Femto Maximum Sensitivity enhanced chemiluminescence substrate working solution was added into each well. The plate was then centrifuged for 5 minutes at 1000 rpm. The luminescence signal was measured using a plate Reader.

Figure 7:
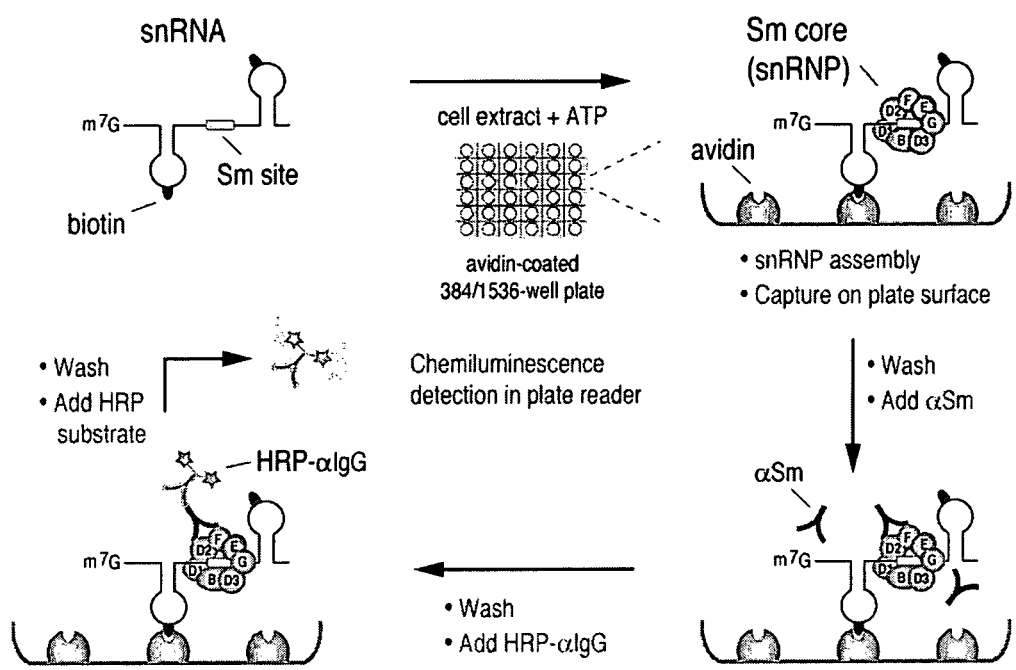
FIG. 7 is a schematic depiction of the assay of the present invention completed in a high-throughput format without magnetic beads for the detection of in vitro assembled snRNPs.
Figure 11:
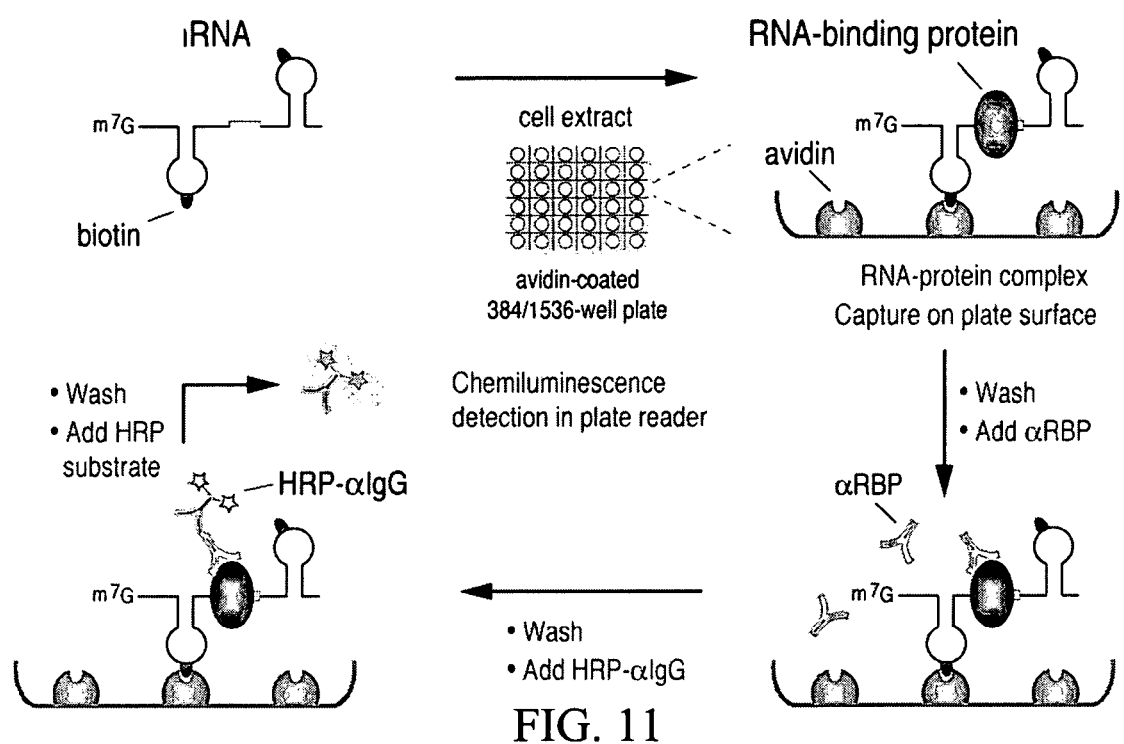
FIG. 11 is a schematic depiction of the assay of the present invention completed in a high-throughput format without magnetic beads for the detection of in vitro RNA binding protein-RNA interactions.
Figure 12:
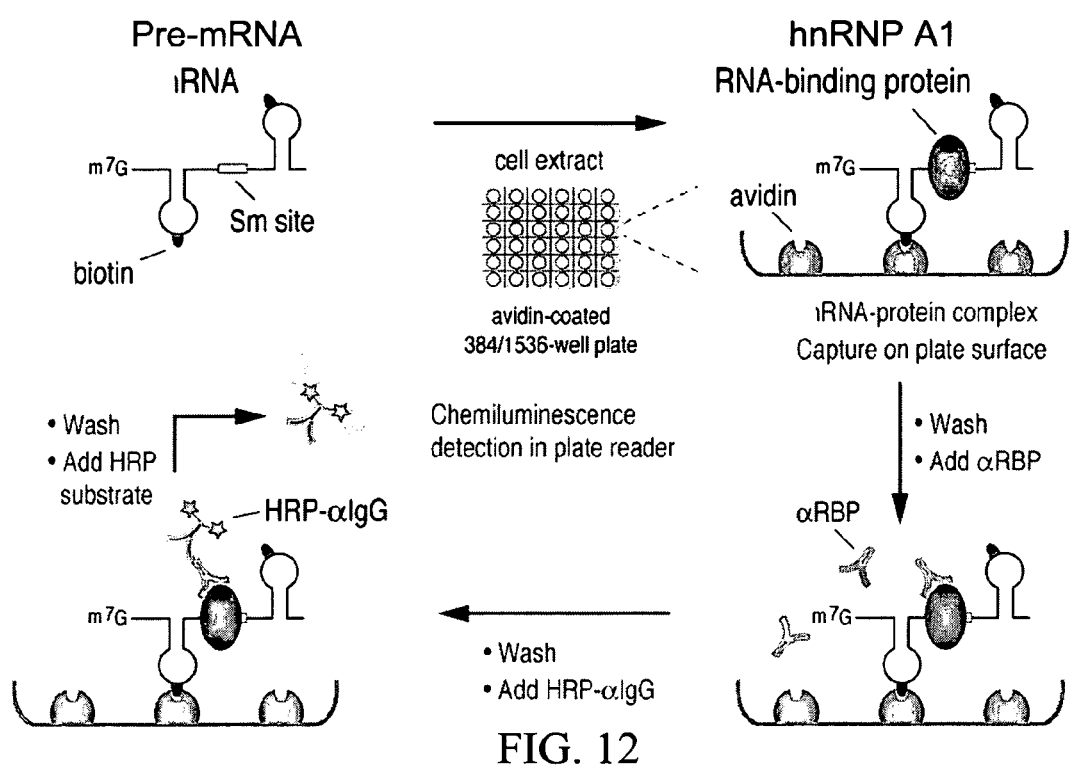
FIG. 12 is a schematic depiction of the assay of the present invention completed in a high-throughput format without magnetic beads for the detection of the in vitro interaction between the RNA binding protein hnRNP A1 with pre-mRNA.
Figure 13:
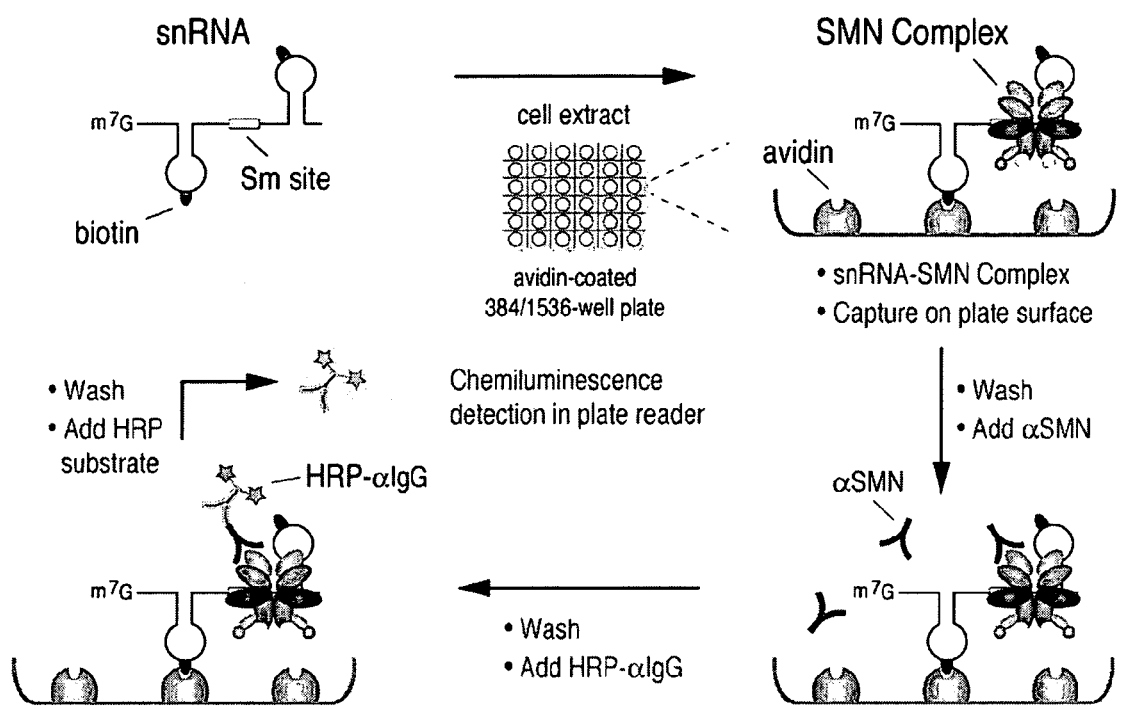
FIG. 13 is a schematic depiction of the assay of the present invention completed in a high-throughput format without magnetic beads for the detection of the in vitro interaction between snRNA and the entire SMN complex.

A schematic illustration of the present assay used to detect Sm core assembly on snRNA is depicted in FIG. 7. A schematic illustration of the assay of the present invention used to detect an RNA binding protein interaction with an RNA is depicted in FIG. 11. A schematic illustration of the assay described herein for the detection of the interaction between hnRNP A1 with pre-mRNA is depicted in FIG. 12. FIG. 13 depicts the assay of the present invention used to detect the interaction between snRNA and the entire SMN complex.

Detection of RNA Binding Protein Inhibitors or Activators

Figure 8A:
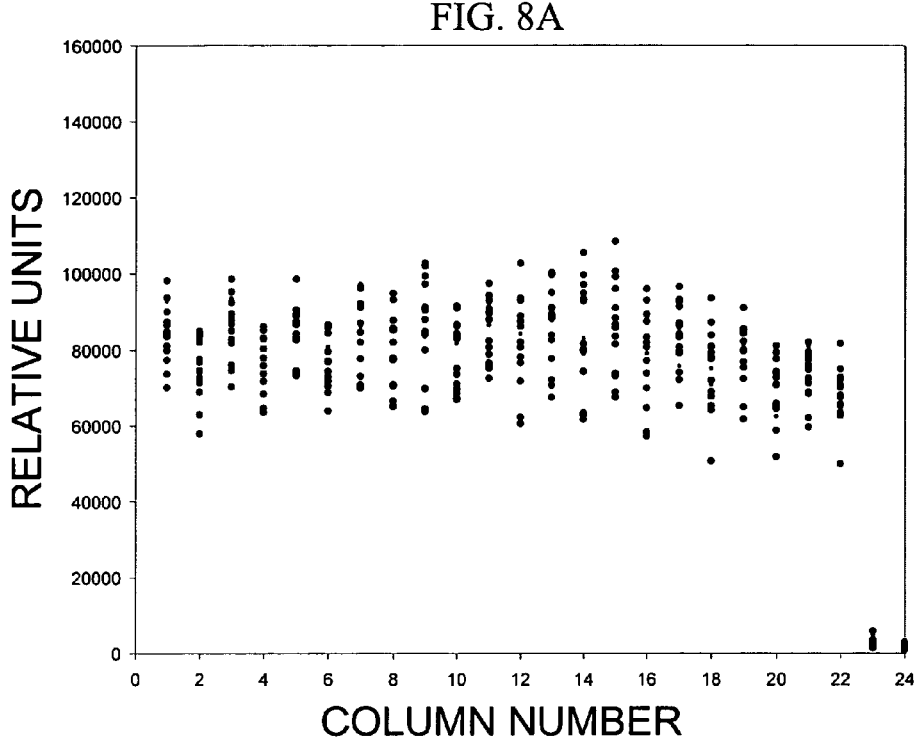
FIGS. 8A and 8B, is a series of scatter plots depicting the results of an SMN complex activity assay in a high-throughput, multi-well (384 well) format. The image depicts a scatter plot of a representative plate.
Figure 8B:
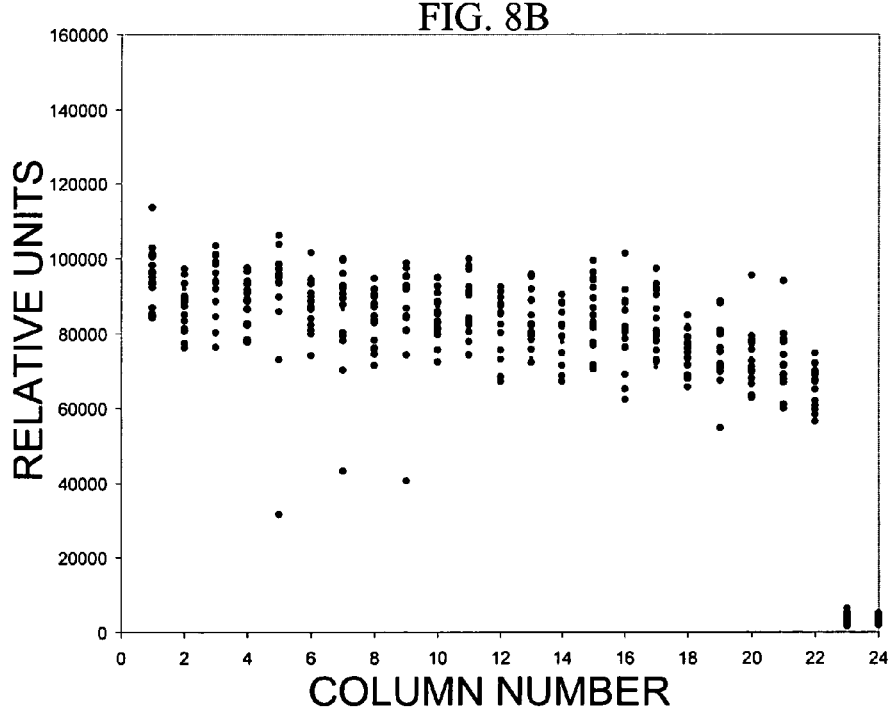

The assays described herein are further useful for identifying a compound that inhibits or activates (i.e. accelerates) the formation of an RNA binding protein-RNA complex. As demonstrated in FIG. 8, the assay of the present invention was performed essentially as described elsewhere herein with either DMSO or various test compounds added to the ATP, cell extract, labeled RNA mixture. Control compounds (DMSO) provide a baseline measurement of RNA binding protein (SMN complex) activity (FIG. 8A). Compounds that inhibit RNA binding protein-RNA interaction produce a lower relative unit of activity than compounds that do not inhibit such activity. Lowered RNA binding protein activity is indicated by relative units lower than the baseline determined with a control compound (FIG. 8B). Increased RNA binding protein activity would be indicated by relative units above the baseline.

Figure 9:
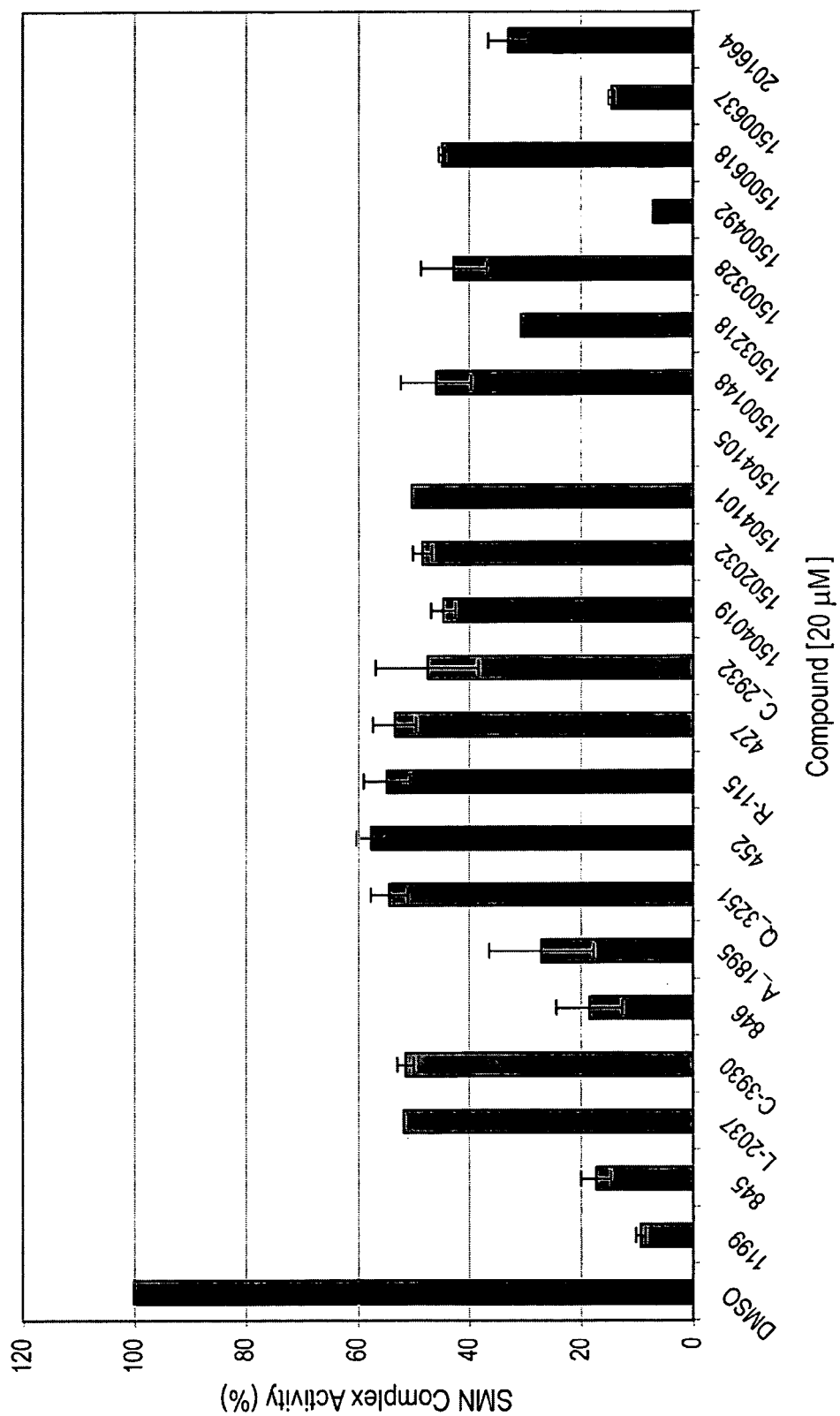
FIG. 9 is a graph depicting the results of an SMN complex activity assay in a high-throughput, multi-well (384 well) format.

Compounds that inhibit RNA binding protein-RNA complex activity are identified using the assay described above. As an example, if a baseline determination is made using a control compound (e.g. DMSO), compounds that, when added to the assay of the present invention, lower the activity of an RNA binding protein-RNA interaction (e.g. the activity of the SMN complex) are inhibitors of RNA binding protein-RNA interactions. Using the assay of the present invention, out of approximately 4000 compounds screened, 22 identified compounds demonstrate inhibition of SMN complex activity (FIG. 9).

Figure 10A:
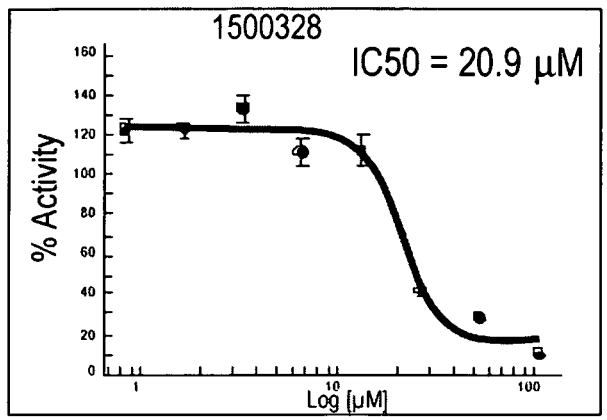
FIGS. 10A and 10B, is a series of images depicting quantitative dose response curves of various inhibitors of SMN complex activity as measured by the assay of the present invention.
Figure 10A:
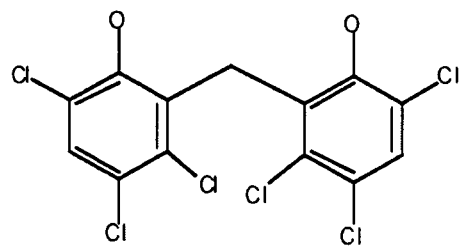
Figure 10A:
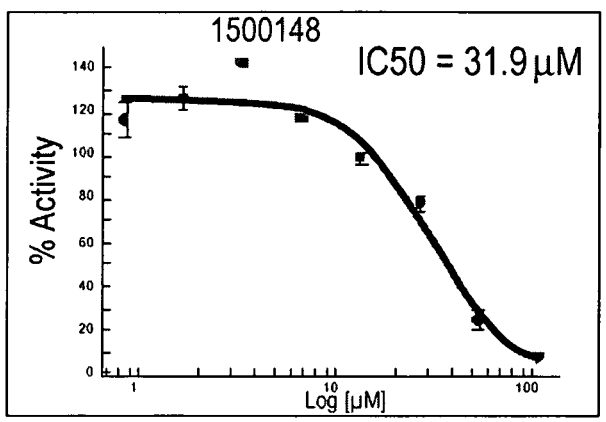
Figure 10A:
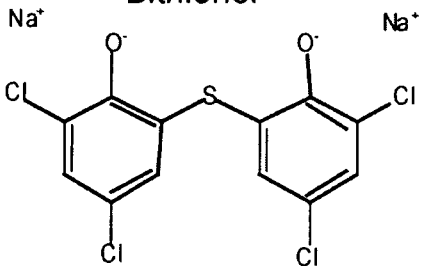
Figure 10A:
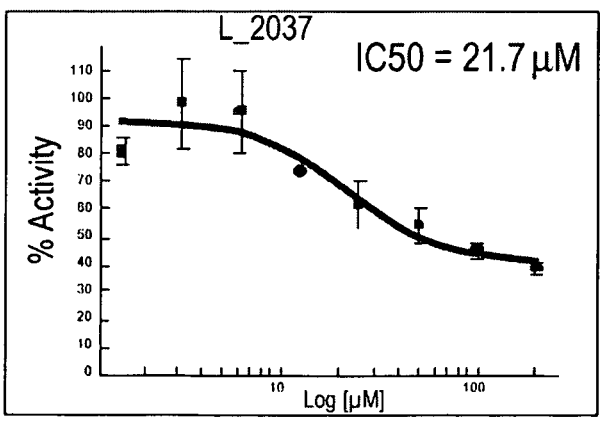
Figure 10A:
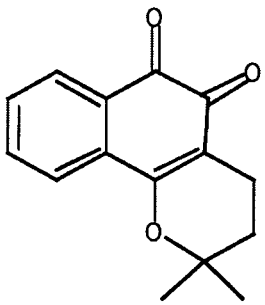
Figure 10B:
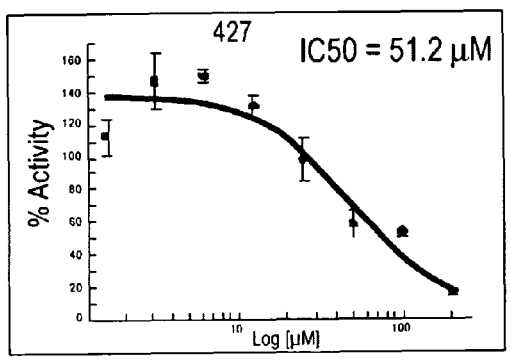
Figure 10B:
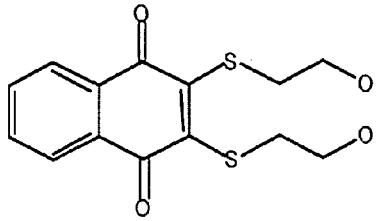
Figure 10B:
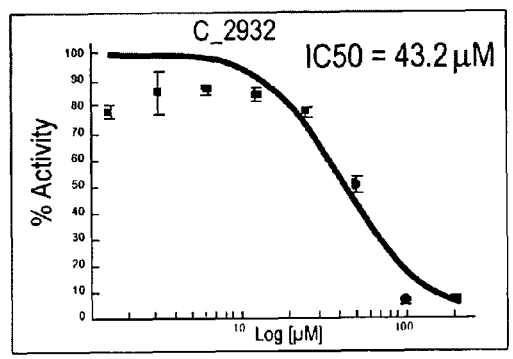
Figure 10B:
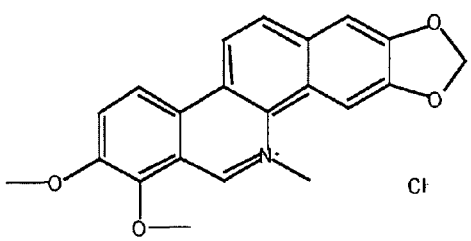
Figure 10B:
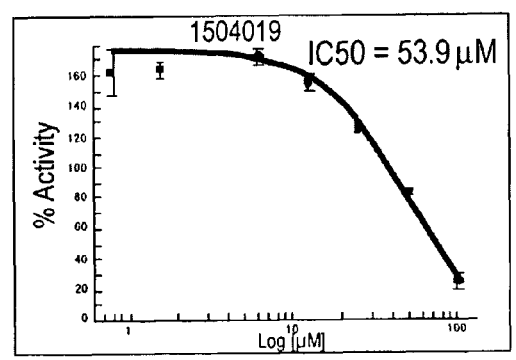
Figure 10B:
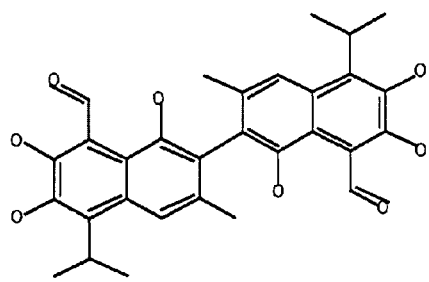

The assay of the present invention can also be used to determine the dose response activity of a compound on an RNA binding protein-RNA complex. Varying the amount of compound added to the assay and comparing the activity as measured by chemiluminescence results in a dose response curve for each compound. Thus, the most active or potent compounds can be identified using the quantitative aspects of the present assay. FIGS. 10A and 10B demonstrate dose response curves and the identity of the inhibitors identified using the assay described herein.

The method described herein is sensitive, quantitative, easy to set up, and readily suitable for laboratory automation. Unlike the methods commonly used so far, RNP gel shift or anti-Sm immunoprecipitation followed by gel electrophoresis, this assay does not require radioactive labeling of the RNAs, nor does it require gel electrophoresis. The biotinylated RNA substrates used for the assay can be prepared ahead of time and stored for many months, allowing off-the-shelf and long-term usage. The assay facilitates detailed studies of the mechanisms of action of the SMN complex and on the process of Sm core assembly. Combined with other approaches, such as RNA interference to systematically reduce protein expression, it is now possible to determine the roles of the Gemins and other components of interest in the assembly reaction. The assay can also be used on extracts from patient cells. The sensitivity of the assay and its co-linearity with the amount of SMN make it suitable as a diagnostic measure of SMA and as a means to identify potential modifiers, both genetic and pharmacological, of the disease phenotype.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An assay to detect presence, amount, and/or activity of a survival of motor neuron (SMN) complex in a cellular extract when said extract comprises an SMN complex, wherein said activity comprises small nuclear ribonucleoprotein particle (snRNP) assembly, said assay comprising:
   a) transcribing a nucleic acid molecule in vitro in the presence of a first label to generate a labeled full length small nuclear RNA (snRNA) molecule;
   b) contacting a substrate with said labeled full length snRNA molecule of step a), wherein said labeled full length snRNA specifically binds to said substrate via said label;
   c) contacting said labeled full length snRNA molecule of step b) with a cellular extract in the presence of adenosine triphosphate (ATP), wherein when said cellular extract comprises a SMN complex, a SMN protein, and Sm proteins comprising B/B', D1, D2, D3, E, F, and G, said Sm proteins bind to said labeled full length snRNA molecule to formulate a complex, an assembled snRNP, comprising said labeled full length snRNA molecule and said Sm proteins;
   d) contacting said complex comprising said labeled full length snRNA molecule and said Sm proteins with a first antibody that specifically binds a RNA binding Sm protein that binds snRNA under stringent conditions in a buffered contacting composition comprising high salt and heparin such that the first antibody binds a snRNA binding Sm protein present in the assembled snRNP in order to determine an amount of Sm proteins that assemble on the snRNA molecule;
   e) contacting said first antibody with a second antibody that specifically binds said first antibody; and
   f) detecting an amount of said second antibody specifically bound to said first antibody, wherein the amount of bound second antibody is indicative of the amount of Sm protein in the assembled snRNP and the amount of Sm protein in the assembled snRNP is indicative of the presence, amount, and/or activity of the SMN complex in the extract,
   wherein, steps b) to f) are performed on the substrate of step b).

2. The method of claim 1, wherein high salt is 500 mM NaCl and heparin is 2 mg/ml heparin.

3. The assay of claim 1, wherein said first label is a non-radioactive label.

4. The assay of claim 3, where said non-radioactive label is biotin.

5. The assay of claim 1, wherein said substrate in step b) comprises a compound selected from the group consisting of avidin and streptavidin.

6. The assay of claim 1, wherein said second antibody comprises a label.

7. The assay of claim 6, wherein said second antibody label is horseradish-peroxidase.

8. The assay of claim 1, wherein detecting said second antibody comprises detecting luminescence.

9. An assay to detect an interaction between snRNA and survival of motor neuron (SMN) complex in a cellular extract when said extract comprises an SMN complex, said assay comprising:
   a) transcribing a nucleic acid molecule in vitro in the presence of a first label to generate a labeled full length snRNA molecule;
   b) contacting a substrate with said labeled full length snRNA molecule of step a), wherein said labeled full length snRNA specifically binds to said substrate via said label;
   c) contacting said labeled full length snRNA molecule of step b) with a cellular extract that is competent for snRNP assembly in the absence of ATP, wherein when said cellular extract comprises a SMN complex, a SMN protein, and Sm proteins comprising B/B', D1, D2, D3, E, F, and G, said SMN complex binds to said labeled full length snRNA molecule to formulate an snRNA-SMN complex comprising said labeled full length snRNA molecule and said SMN complex;
   d) contacting said snRNA-SMN complex with a first antibody that specifically binds said snRNA-SMN complex;
   e) contacting said first antibody with a second antibody that specifically binds said first antibody; and
   f) detecting said second antibody when said second antibody is specifically bound to said first antibody,
      thereby detecting the interaction between snRNA and SMN complex,
      wherein, steps b) to f) are performed on the substrate of step b).

* * * * *